US010076655B2

(12) United States Patent
Paul et al.

(10) Patent No.: US 10,076,655 B2
(45) Date of Patent: Sep. 18, 2018

(54) VESTIBULAR STIMULATION SYSTEM

(75) Inventors: Zachary D. Paul, Pittsburgh, PA (US);
Stefanie Lattner, Gibsonia, PA (US);
Benjamin A. Giovannelli, Delmont, PA (US); Michael E. Colbaugh, Trafford, PA (US); Todd Kirby, Spring Church, PA (US); Kevin Wells, Saltsburg, PA (US); William H. Broadley, Pittsburgh, PA (US); Al Vangura, Gibsonia, PA (US); Michael Cessna, McKees Rocks, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1299 days.

(21) Appl. No.: 12/211,275

(22) Filed: Sep. 16, 2008

(65) Prior Publication Data

US 2009/0082831 A1 Mar. 26, 2009

Related U.S. Application Data

(60) Provisional application No. 60/974,136, filed on Sep. 21, 2007.

(51) Int. Cl.
*A61N 1/36* (2006.01)
*A61N 1/04* (2006.01)
*A61N 1/365* (2006.01)

(52) U.S. Cl.
CPC ......... *A61N 1/0456* (2013.01); *A61N 1/0472* (2013.01); *A61N 1/36014* (2013.01);
(Continued)

(58) Field of Classification Search
CPC .. A61N 1/0456; A61N 1/0484; A61N 1/0526; A61N 1/0541; A61N 1/36032;
(Continued)

(56) References Cited

U.S. PATENT DOCUMENTS 1,336,859 A * 4/1920 Reihing ............... H01B 7/06
  379/438
3,134,861 A * 5/1964 Dempsey ............. H04R 1/105
  381/151

(Continued)

FOREIGN PATENT DOCUMENTS

WO   2008028063 A2   3/2008

OTHER PUBLICATIONS

Fitzpatrick et al. "Probing the human vestibular system with galvanic stimulation". Journal of Applied Physiology Published Jun. 1, 2004 vol. 96 No. 6, 2301-2316, DOI: 10.1152/japplphysiol.00008. 2004.*

(Continued)

*Primary Examiner* — Eugene T Wu
(74) *Attorney, Agent, or Firm* — Michael W. Haas

(57) ABSTRACT

A vestibular stimulation system and method that includes a housing, a power supply disposed in the housing, an electrode assembly adapted to be coupled to the housing, and a controller disposed in the housing and operatively coupled to the power supply. The controller controls the delivery of energy from the power supply to the electrode assembly. An input element is also disposed on an exterior surface of the housing. The input element is manually manipulated to control the operation of the vestibular stimulation system. A display disposed on an exterior surface of the housing provides visual information regarding the operation of the vestibular stimulation system. A mounting assembly is coupled to the housing to mount the housing on such a user.

22 Claims, 21 Drawing Sheets

(52) U.S. Cl.
CPC ..... *A61N 1/36032* (2013.01); *A61N 1/36036* (2017.08); *A61N 1/36535* (2013.01); *A61N 1/36542* (2013.01); *A61N 1/0484* (2013.01); *A61N 1/0492* (2013.01)

(58) Field of Classification Search
CPC ...... A61N 1/36025; A61N 2001/36039; A61B 5/6803; A61B 5/6814; A61B 5/6815
USPC .......................... 607/62, 139–140, 149–150; 600/383–384, 386, 388–390; 2/171, 2/171.2
See application file for complete search history.

(56) References Cited

U.S. PATENT DOCUMENTS

| | | | | |
|---|---|---|---|---|
| 3,300,572 | A | * | 1/1967 | Dahlgren ................. H01B 7/06 174/69 |
| 3,488,431 | A | * | 1/1970 | Nixon .................. H01B 7/0009 174/70 R |
| 3,809,800 | A | * | 5/1974 | Fletcher ................... H01B 5/02 174/69 |
| 4,305,402 | A | * | 12/1981 | Katims ......................... 600/554 |
| 4,524,773 | A | * | 6/1985 | Fischell et al. ................. 607/58 |
| 4,558,703 | A | | 12/1985 | Mark |
| 4,727,599 | A | * | 2/1988 | Rappaport ............. A42B 1/245 2/DIG. 11 |
| 4,918,757 | A | * | 4/1990 | Janssen et al. .................... 2/171 |
| 4,947,832 | A | * | 8/1990 | Blitzer ............................ 601/56 |
| 5,044,362 | A | | 9/1991 | Younes |
| 5,107,830 | A | | 4/1992 | Younes |
| 5,304,209 | A | * | 4/1994 | Adams et al. .................. 607/30 |
| 5,514,175 | A | * | 5/1996 | Kim et al. .................... 607/136 |
| 5,535,738 | A | | 7/1996 | Estes et al. |
| 5,708,725 | A | * | 1/1998 | Ito ........................ H04R 1/1041 381/370 |
| 5,758,651 | A | | 6/1998 | Nygard et al. |
| 5,794,615 | A | | 8/1998 | Estes |
| 5,809,573 | A | * | 9/1998 | Bary ........................ A61F 7/03 128/866 |
| 5,814,095 | A | | 9/1998 | Muller et al. |
| 6,077,237 | A | * | 6/2000 | Campbell ............... G06F 3/011 600/587 |
| 6,105,575 | A | | 8/2000 | Estes et al. |
| 6,145,131 | A | * | 11/2000 | Huff ........................ A41D 23/00 2/171 |
| 6,171,258 | B1 | * | 1/2001 | Karakasoglu ........ A61B 5/0205 600/529 |
| 6,219,578 | B1 | * | 4/2001 | Collins et al. ..................... 607/2 |
| 6,228,021 | B1 | | 5/2001 | Kania |
| 6,301,367 | B1 | * | 10/2001 | Boyden .................. A42B 1/245 2/209 |
| 6,314,324 | B1 | | 11/2001 | Lattner et al. |
| 6,496,734 | B1 | | 12/2002 | Money |
| 6,546,291 | B2 | * | 4/2003 | Merfeld et al. ................. 607/62 |
| 6,609,517 | B1 | | 8/2003 | Estes et al. |
| 6,748,275 | B2 | | 6/2004 | Lattner et al. |
| 6,932,084 | B2 | | 8/2005 | Estes et al. |
| 7,016,733 | B2 | | 3/2006 | Dublin et al. |
| 7,650,007 | B2 | * | 1/2010 | Iuliis ........................ A45F 5/00 381/374 |
| 7,856,275 | B1 | | 12/2010 | Paul et al. |
| 2003/0135248 | A1 | * | 7/2003 | Stypulkowski ................ 607/73 |
| 2003/0195588 | A1 | | 10/2003 | Fischell et al. |
| 2003/0199945 | A1 | | 10/2003 | Ciulla |
| 2004/0073275 | A1 | * | 4/2004 | Maltan et al. ................... 607/57 |
| 2004/0218039 | A1 | * | 11/2004 | Cooper .................... A61B 1/05 348/66 |
| 2005/0148897 | A1 | * | 7/2005 | Cho ...................... A61B 5/0031 600/533 |
| 2005/0222641 | A1 | * | 10/2005 | Pless .............................. 607/45 |
| 2007/0135862 | A1 | * | 6/2007 | Nicolai et al. .................. 607/56 |
| 2008/0300519 | A1 | * | 12/2008 | Helt et al. ........................ 601/47 |
| 2010/0042180 | A1 | * | 2/2010 | Mueller ............... A61N 1/0456 607/46 |

OTHER PUBLICATIONS

Kageyama, Yuri. "A remote control that controls humans". Associated Press, updated Oct. 25, 2005. Accessed Apr. 3, 2015. <http://www.nbcnews.com/id/9816703/ns/technology_and_science-innovation/>.*
U.S. Appl. No. 11/327,062, Paul et al.
U.S. Appl. No. 60/841,802, Colbaugh et al.
Fitzpatrick, R. et al. entitled "Probing the Human Vestibular System with Galvanic Stimulation", J. Appl. Physiol. Jun. 2004, vol. 96, pp. 2301-2316.

* cited by examiner

| Icon Image | Description |
|---|---|
|  | Low Battery Indicator (Flashes) |
|  | Partially Full Battery Indicators |
|  | Full Battery Indicator |
|  | Therapy Leads Disconnected from User or Device Electronics Enclosure — used to inform the user that therapy was stopped because the therapy leads were disconnected |
|  | Motion Detected — used to inform the user that therapy was stopped due to excess device motion ensuring user safety while wearing the device |
|  | Setup Menu (flashes): Only permits adjustments for user preference/comfort: enable/disable of audio information tones and selection of high/low backlight intensity. |
|  | Audio Information Tones Muted |
|  | Therapy Active Indicator: used to indicate therapy is being delivered by sweeping back and forth at the same rate as the therapy. When the indicator is not sweeping no therapy is being delivered. |
|  | Therapy Level Indicator: used to indicate the user selected therapy level (1 = 0.1mA; 2 = 0.2mA; 3 = 0.3mA; 4 = 0.4mA; 5 = 0.5mA; all peak values) When flashing it indicates the therapy amplitude is ramping up but has not reached the full selected therapy level. (Ramp up: 0.5, 2, 5 or 10 minutes) |

FIG. 3

VESTIBULAR STIMULATION SYSTEM

CROSS-REFERENCE TO RELATED APPLICATIONS

This application claims priority under 35 U.S.C. § 119(e) from provisional U.S. patent application No. 60/974,136, filed Sep. 21, 2007, the contents of which are incorporated herein by reference.

BACKGROUND OF THE INVENTION

1. Field of the Invention

The present invention pertains to a vestibular system and method of operating such as system to maximize the effectiveness of the therapy and the comfort to the user, while making the treatment as easy as possible.

2. Description of the Related Art

The vestibular system is responsible for the detection of the position and motion of the head in space. The semicircular canals and otolythic organs, which are located in the inner ear, are the sensory organs of the vestibular system and collect head position and motion information and transmit it to the central nervous system via the eighth cranial nerve.

Stimulation of either the semicircular canals and/or otolythic organs, the nerve fibers leading from these organs, or the eighth cranial nerve results in a sensation of movement in normal subjects. Disorders of the vestibular system may result in such physiological disorders as dizziness, vertigo, and nausea with symptoms ranging in severity from mild to completely debilitating. However, moderate stimulation of the vestibular system may cause perceptions of mild movement that are not unpleasant, but can rather have beneficial properties such as promoting sleep or to help relaxation.

The vestibular system may be stimulated in a variety of manners, including calorimetrically, chemically, mechanically (e.g., pressure, tilt, acceleration, acoustic, etc.), and electrically. Among these approaches, electrical stimulation provides the most flexibility in terms of patterns of stimulation, convenience, and comfort for the patient. In order to stimulate the vestibular system electrically, a stimulation waveform must delivered to the vestibular system. This is typically accomplished by providing a surface electrode that is placed in, on, or near one ear of the user. A second electrode is also placed on the patient to provide a complete circuit. This second electrode can be placed near the first electrode, near the other ear, or somewhere else on the head. A stimulation unit generates and delivers the stimulation energy to the stimulation electrode.

While this concept is simple to conceptualize, providing an apparatus that allows the patient to fall asleep and sleep comfortably without becoming tangled in electrical wires or having their sleep disrupted by a bulky stimulation unit is a significant challenge. There are also numerous challenges in delivering stimulation energy in a safe and effective fashion.

SUMMARY OF THE INVENTION

In accordance with the present invention, there is provided an apparatus for the stimulation of the vestibular system. The apparatus includes a housing, a power supply disposed in the housing, an electrode assembly adapted to be coupled to the housing, and a controller disposed in the housing and operatively coupled to the power supply. The controller controls delivery of energy from the power supply to the electrode assembly. An input element is disposed on an exterior surface of the housing. The input element is manually manipulated to control the operation of the vestibular stimulation system. A display is also disposed on an exterior surface of the housing to provide visual information regarding the operation of the vestibular stimulation system. A mounting assembly mounts the housing on such a user.

In a further embodiment, a method of providing vestibular stimulation to a user is provided. This method includes providing a vestibular stimulation system that includes (1) a housing, (2) a power supply disposed in the housing, (3) a controller disposed in the housing and operatively coupled to the power supply to control delivery of energy from the power supply to the electrode assembly, (4) an input element disposed on an exterior surface of the housing, and (6) a display disposed on an exterior surface of the housing. This method further includes coupling an electrode assembly to the housing, mounting the housing on such a user using a mounting assembly coupled to the housing, and delivering stimulation energy to a user by providing energy from the power supply to the electrode assembly. The method further includes controlling the operation of the vestibular stimulation system by manually manipulating the input element, and providing visual information regarding the operation of the vestibular stimulation system using the display.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 3 illustrates various icons that are capable of being displayed by the vestibular stimulation system;

DETAILED DESCRIPTION OF THE EXEMPLARY EMBODIMENTS

I. System Architecture/Hardware

Figure 1:
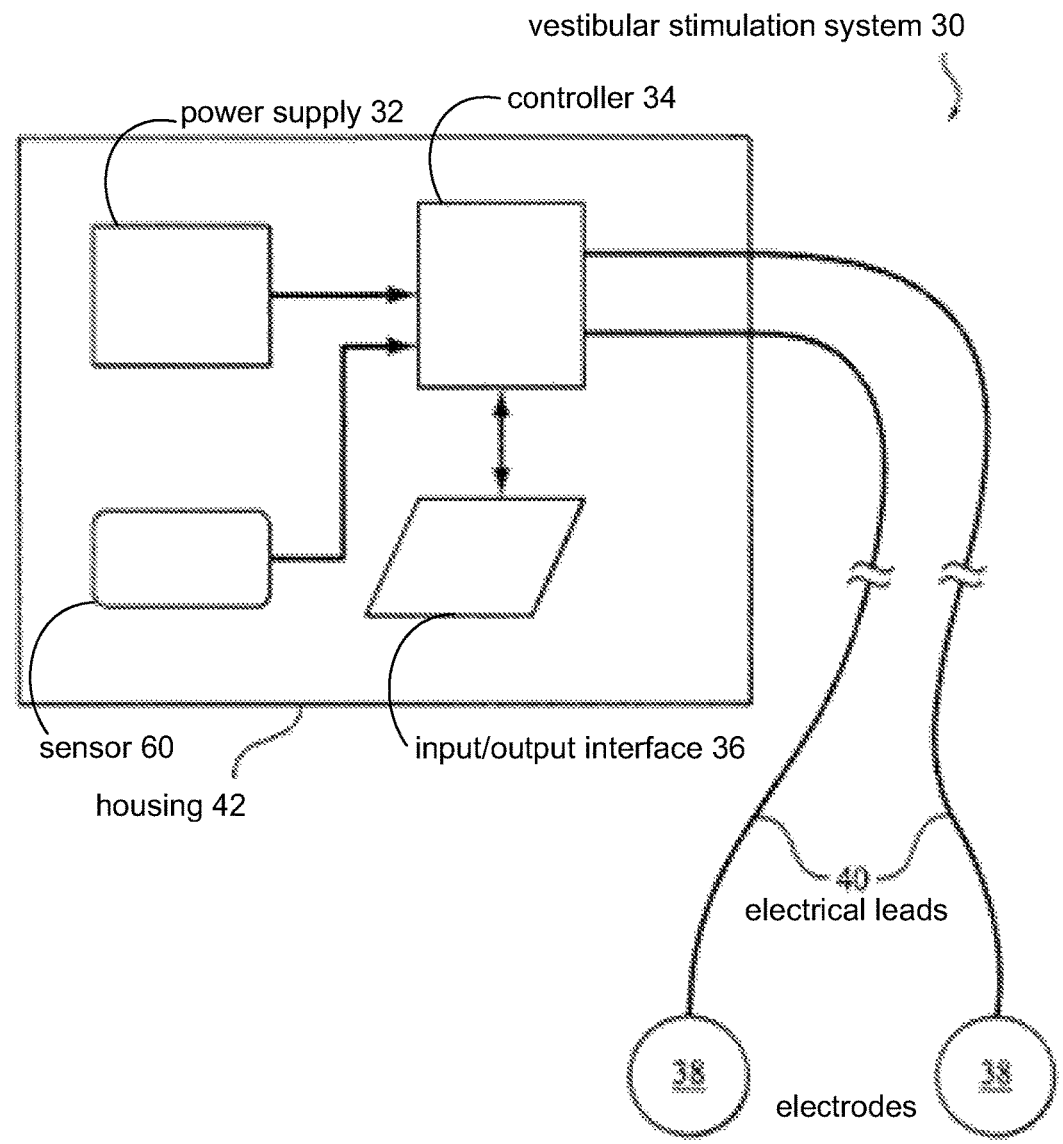
FIG. 1 is a schematic diagram of a vestibular stimulation system according to the principles of the present invention.
Figure 2:
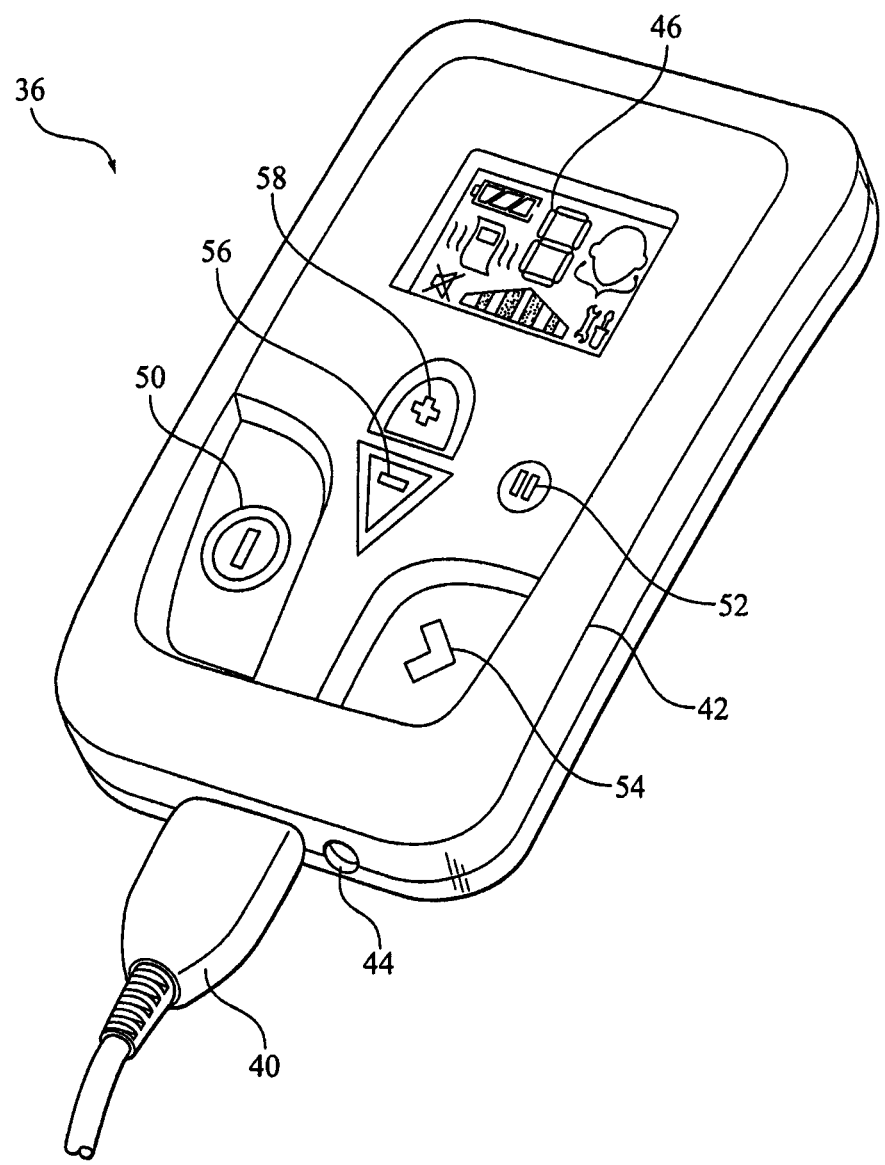
FIG. 2 is a perspective view of a stimulation controller for use in the vestibular stimulation system according to the principles of the present invention.

Referring now to FIGS. 1 and 2, the basic components of a vestibular stimulation system 30 according to the principles of the present invention will now be described. Vestibular stimulation system 30 includes a power supply 32, a controller 34, an input/output interface 36, and a pair of electrodes 38. Wires or electrical leads 40 couple the controller and/or power supply to the electrodes. The electrical leads and the electrodes that are coupled to the electrical leads in either a fixed or removable fashion, are referred to as the electrode assembly.

As discussed in greater detail below, vestibular stimulation system 30 also includes one or more optional sensors 60, such as temperature, light, sound, motion, acceleration, position, EMG, EOG, ECC, pulse oximetry, heart rate, sleep state, rapid eye movement (REM), galvanic skin sensor, nerve activity, sweat detectors, vessel constriction or dilatation sensors, or other sensors that provide information to the controller. Power supply 32 is any source of power, such as an AC power supply or a DC power supply, e.g., batteries, solar cells, etc. Controller 34 includes the electronic components that are required to deliver an electrical stimulus to the electrodes.

In the illustrated exemplary embodiment, vestibular stimulation system 30 is a portable, battery-powered device that provides a minor electrical current to electrodes 38, which are disposed on the user near the vestibular system. More specifically, one electrode is disposed behind on the mastoid so that the current travels through the user between the electrodes. The other electrode can be disposed on the opposite side of the patient near the other vestibular system or anywhere on the head or elsewhere on the user's body, such as the shoulder, back, or neck, to serve as a reference or ground electrode.

The electrical current is delivered in a manner so as to evoke the sensation of rocking or floating to promote somnolence (sleepiness). In an exemplary embodiment the electrical current is delivered as a sinusoidal wave having an amplitude in a range of 0.1 mA to 1.0 mA peak to peak and a frequency in a range of 0.1 to 1.0 Hz. The present invention contemplates allowing the physician, authorized technician, i.e., caregiver, and/or the patient/user to set parameters of amplitude (stimulation level) and duration (frequency) of the stimulation signal.

The present invention contemplates the use of higher amplitude electrical current to evoke the sensation in less sensitive subjects, depending on the electrode type and/or placement, or to generate a desired result for a given subject at a particular frequency or other stimulation signal characteristic. For example, the present inventors determined that approximately 85% of users experience a noticeable, i.e., a perceivable, vestibular stimulation with an output current range of 0.1 to 1.0 mA using a 0.5 Hz Sine wave signal applied to the stimulation electrodes. When an ear bud or ear spiral electrode is used, a stimulation of 1.5-2.0 mA peak amplitude is able to product a perceivable vestibular stimulation in approximately 100% of the population.

The stimulation site allows the vestibular nerves in the inner ear to receive this input and provide a sensory nerve output to the brain that results in user sway (rocking) and ultimately relaxation leading to somnolence. U.S. Pat. No. 6,314,324 ("the '324 patent") and U.S. Pat. No. 6,748,275 ("the '275 patent"), the contents of each of which are incorporated herein by reference, teach a technique for stimulating the vestibular system to induce a rocking sensation that is suitable for use as the stimulation therapy provided by vestibular stimulation system 30.

In an exemplary embodiment, power supply 32 and controller 34 are disposed in a common housing 42, with the electrical leads extending from the housing. However, the present invention also contemplates that the power supply may be separate from the housing containing the controller. For example, the present invention contemplates using an inductive field method of providing power to the components of the system mounted in the user. For example, a magnetic and/or electric field at radio frequencies can be used to power vestibular stimulation system 30. In addition, an RF link can be used to implement a full-duplex data communication link between the powering source and the other components of the vestibular stimulation system. Powering the device remotely, and providing a wireless link to communicate commands remotely to the device from a remote controller, potentially from a bedside unit such as an alarm clock control system, PDA, or personal computer, provides a convenient and/or robust user interface system that can be tailored to match the needs of the system, the user, or both.

Housing 42 can be made from any suitable material, such as cleanable ABS/poloycarbonate plastic. For present purposes, the housing containing the components that control the application of the stimulation energy is referred to as the "control unit" and is indicated generally by reference numeral 70. Thus, in the embodiment of FIGS. 1, 2, and 5, housing 42 is also referred to and is indicated as control unit 70.

In the embodiment shown in FIG. 2, the power source is an internal rechargeable battery contained in housing 42. An example of a suitable battery is a 3.7 V DC rechargeable Li-ion coin cell batter. A terminal 44 is provided on the housing for connecting a battery recharger (not shown) to the batteries in the housing. In an exemplary embodiment, the time needed to recharge the battery for one hour of use from a drained state is not greater than 15 minutes. The entire assembly, i.e., the housing including the batteries, but without the electrical leads attached, weighs less than 50 grams, and has the following dimensions 0.75 inch height, 3.3 inch length, and 1.88 inch width. Thus, the volume occupied by the housing is approximately 4.7 in$^3$ (11.94 cm$^3$) and, in particular, 4.653 in$^3$ (11.82 cm$^3$). The volume to weight ratio is not greater than approximately 0.2388 cm$^3$/g.

In its most simple form, controller 34 is a manually actuated device, for example an on/off switch. In more sophisticated embodiments, the controller is a processor that regulates the amount of energy and/or the pattern of the energy delivered from source 32 to electrodes 38. The controller can include a processor, circuit, memory, programming, and other electrical, software, and/or electromechanical elements necessary to control the energy provided to the electrodes.

Electrodes 38 are any electrodes suitable for delivering stimulating energy to the vestibular system of the user. The electrodes can be invasive, i.e., disposed under the skin of the user, or non-invasive. Examples of non-invasive or surface electrodes are disclosed in U.S. provisional patent application No. 60/841,802 ("the '802 application"), and U.S. patent application Ser. No. 11/327,062 ("the '062 application), the contents of each of which are incorporated herein by reference. Electrical leads 40 are flexible wires that are either fixed or removably attached to housing 40 and/or electrodes 38. When removable, a connector terminal is provided in the exposed surface of the housing to which the electrical leads are coupled.

As shown in detail in FIG. 2, the input/output interface, which is generally indicated by reference numeral 36 in this figure, includes indicators and manually actuated elements provided on an exterior surface of housing 42. More specifically, input/output interface 36 includes a display 46 and several manually actuatable buttons or keys, the details of which are discussed below. In an exemplary embodiment, display 46 is a backlit LCD and the buttons, the display, or both are recessed from the surface of the housing to prevent them being accidentally or inadvertently actuated or damaged. The shape, texture, or both of each button can be unique to that button to enable the user to identify a particular button by it feel. One of more of the buttons or features on the button can also be lighted, e.g., backlit, so that they can be seen in a dark room.

Button 50 is used to manually turn the system on and off. Depressing this button toggles the device on or off. Button 52 is used to activate a setup menu, select adjustments that are made, for example using the setup menu, and to exit the setup menu. Button 54 is a "Start Therapy" device. It is used to stop the therapy by depressing this key for at least 2 seconds. Button 56 is a "Decrease Therapy Level Setting". It used to reduce the amount of stimulation energy being delivered to the patient. This can be done, for example, by decreasing the amplitude or peak to peak value of the sine wave. Button 56 is also used to disable the audio or decrease backlight intensity when the setup menu is active. Conversely, button 58 is an "Increase Therapy Level Setting". It is used to increase the amount of stimulation energy being delivered to the patient. This can be done, for example, by increasing the amplitude or peak to peak value of the sine wave. Button 58 is also used to enable the audio or increase backlight intensity when the setup menu is active.

FIG. 3 is a chart illustrating some of the exemplary embodiments for icons that are capable of being shown in display 46. The left column shows the icon and the right column give a short description of the meaning of the icon. It should be noted that the present invention contemplates that display 46 can be an interactive interface, such as a touch screen, where the entire display or portions of the display function as an input device by being touched by a body part, typically a finger, or stylus.

The present invention also contemplates that input/output interface 36 includes a communication link with an external device. Thus, a remote control device can be used to activate/deactivate the stimulation, change control settings, or perform any other function provided by the input/output interface. If a remote control device is used, the user control interface on the device worn by the user can be eliminated. The use of a remote control is especially desirable in the embodiment of the vestibular stimulation system in which the controller is mounted on the user such that user cannot easily see the controller. For example, in the embodiments shown in FIGS. 6-17 the vestibular stimulation system is mounted on the user's head. Providing a remote control that the user can keep at the bedside provides ease of use in controlling the vestibular stimulation system.

The communication links suitable for use in providing data, information, commands or the like, include hardwired or wireless links, such as a modem, a radio frequency (RF) link, an infrared (IR) link, a blue tooth, an RS-232 or similar connection, a USB or similar connection, or any other technique for exchanging or providing data, information, commands, or any combination thereof between two devices. The present invention further contemplates that input/output interface 36 can be other forms of data communication techniques, such as RFITD, smart card, memory stick, or other data storage devices, to transfer data to or from vestibular stimulation system 30.

The present invention also contemplates that the input/output interface includes a speaker or other form of auditory device in or on housing 42. The sound generating device produces auditory signals to inform the user about the device function, for example, an audible signals to indicate some type of information to the user, such as the therapy is being provided, the device is on, the device has been turned on or off, a malfunction or error has occurred, the electrical leads, the electrodes, or both are not connected properly, the electrodes are not on the user or not correctly on the user, the battery is low, or any other for information.

The stimulation energy generating components can be provided in a various types of configurations. For example, they can be integrated into one housing or separated into individual components. For example, if the power supply is a battery, the battery can be separated from the portion of the system containing the controller. These individual components can be modular, i.e., capable of being joined together to form a unitary assembly. Examples of various combinations for mounting the components of the vestibular system are shown for the purposes of illustration, and are by no means meant to be limiting.

Control unit 70 can be mounted on the user in a variety of locations. In an exemplary embodiment of the present invention, the control unit is clipped or attached to the user or the user's clothing, such as the belt using a belt clip, as well know in the art of cell phones and pagers.

Figure 4:
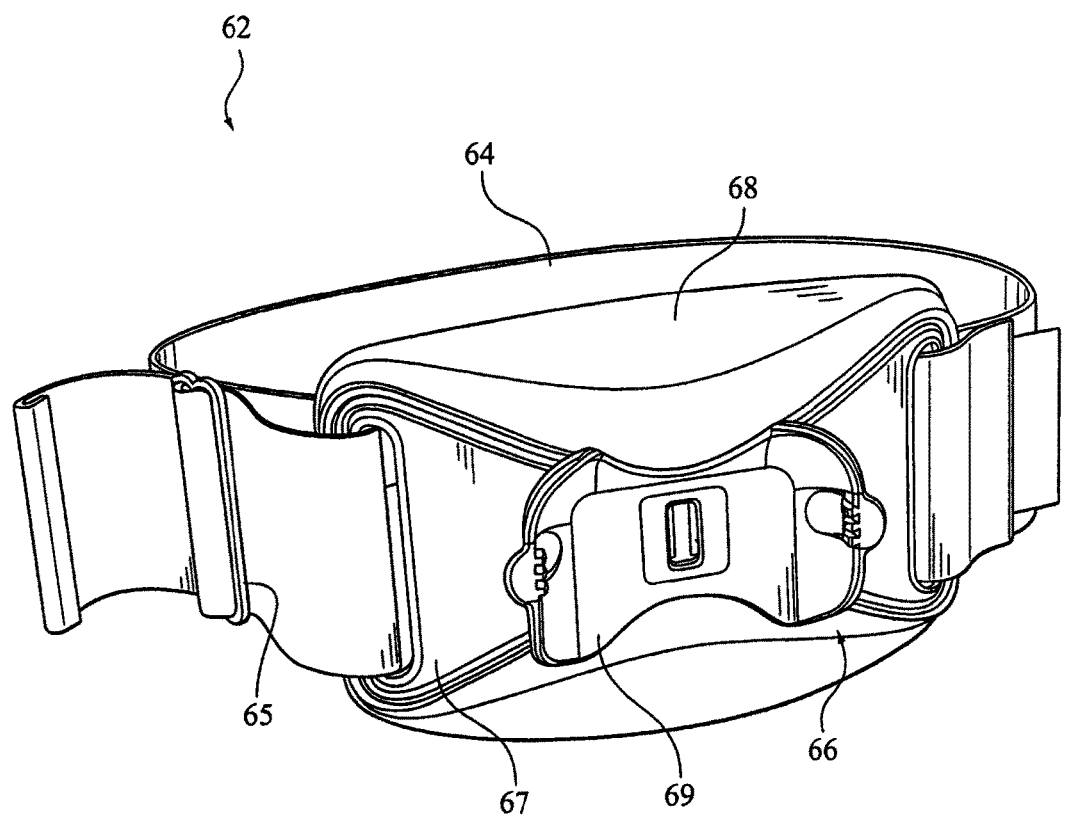
FIG. 4 is a perspective view of an armband for supporting one or more components of the vestibular stimulation system of the present invention on the user.

FIG. 4 illustrates an exemplary embodiment in which an arm band 62 supports housing 42 (controller 70) on the user. Arm band 62 includes a flexible band 64, a rigid or semi-rigid support portion 66, and a padding 68 that protects the user from the support portion. The length of flexible band 64 can be adjusted using any conventional technique. In the illustrated embodiment, a D-ring 65 is provided through which the flexible band is passed.

Support portion 66 and housing 42 are configured such that they selectively attach to one another. For example, clips, taps, grooves, locking pins, detents, or other elements can be provided on support portion 66, housing 42, or both to facilitate the attachment of these two components. The shape, size, and/or configuration of support portion 66, housing 42, or both can be such that two components selectively attach to one another. In the illustrated exemplary embodiment, support portion 66 includes a horse-shoe or cup shaped receptacle 69 that receives a portion of housing 42 and a rigid or semi-rigid mounting member 67 that is coupled to padding 68 and cup shaped receptacle 69. Flexible band 64 is coupled to mounting member 67 via slots provided at each end of the mounting member.

Figure 5:
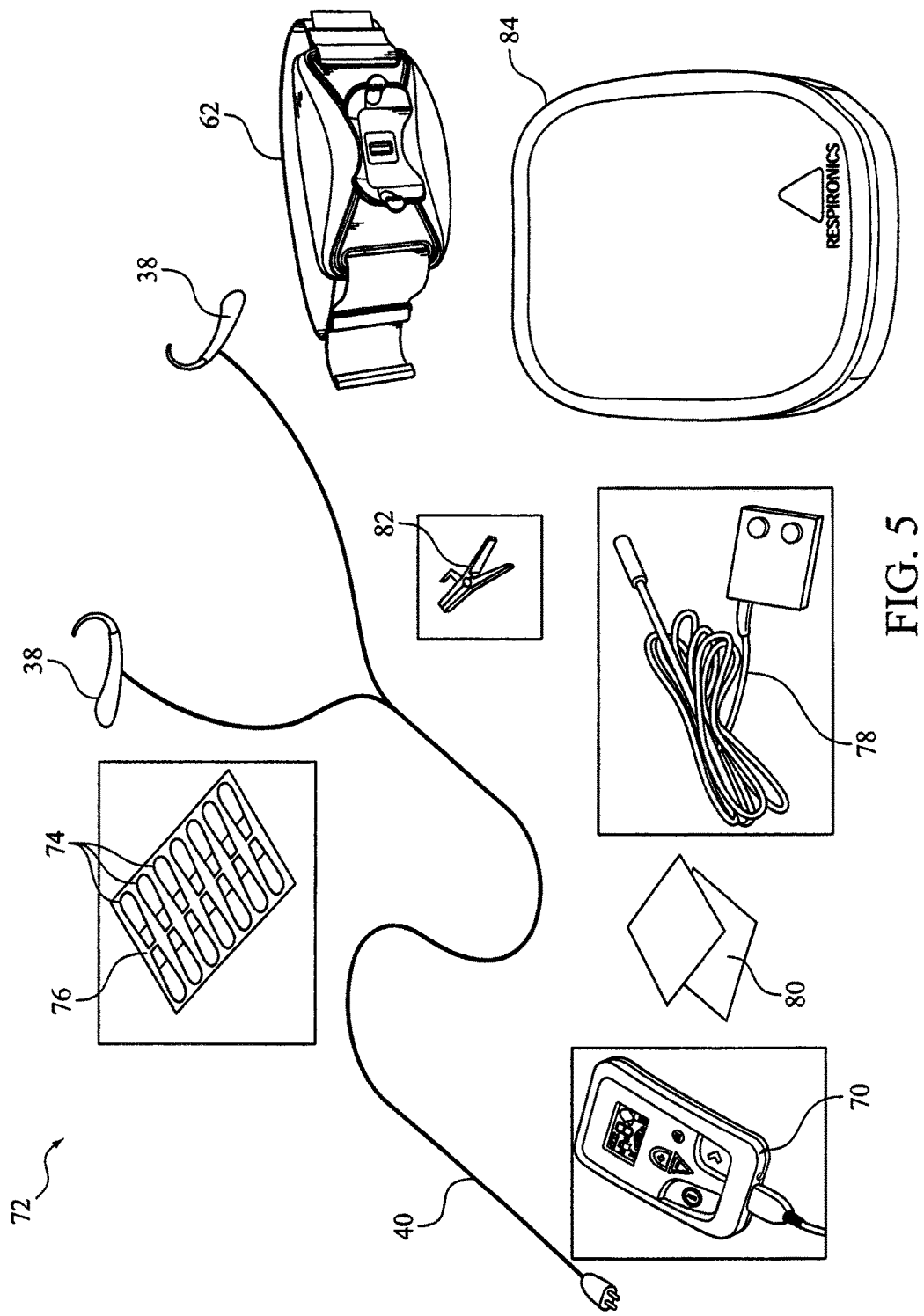
FIG. 5 illustrates a kit containing the components of the vestibular stimulation system according to the principles of the present invention.

The present invention contemplates that the vestibular stimulation system is available to the user as a kit 72, as shown, for example, in FIG. 5. Kit 72 includes vestibular stimulation system 30, which includes housing 42 (control unit 70), electrical leads 40 and electrodes 38. In this embodiment, the electrodes corresponds to the electrodes disclosed in the '802 application. As taught by this application, the electrodes are held on the user via a hydrogel element 74 that is provided over the conducting portion of the electrode. Generally, a new hydrogel element is used each therapy session. Thus, kit 72 includes a supply or plurality of disposable hydrogel elements 74. In the illustrated embodiment, the plurality of disposable hydrogel elements are provided on a sheet 76. However, the present invention contemplates that the hydrogel elements can be supplied in other ways, such as on a roll or in individual packets.

Kit 72 further includes a battery charger 78 and armband 62. The kit also includes a supply of skin preparation pads 80, such as Sali-Wipes™ that are used to prepare the site on the user where the electrodes are to be applied. A clip 82 is also provided for use in managing electrical leads 40. For example, clip 82 is used to clip the electrical lead(s) and/or the stimulation system to the bedding, pillow, or clothing of the user. Finally, kit 72 includes a case 84 that contains the components noted above. Directions for using the system and one or more batteries can also be included in the kit.

As noted above, hydrogel element 74 are one of the few items that are not intended to be reused. Therefore, the present invention contemplates providing replacement kits of hydrogel elements. Included in the package of replacements would be a plurality of hydrogel elements 74 mounted on a releasable/carrier backing and stored in a resealable, vapor-tight (water-tight) bag. However, other techniques for packaging the hydrogel elements are contemplated by the present invention. The hydrogel element replacement kit could also include a supply of skin preparation pads and directions for replacing the hydrogel elements.

As also noted above, the present invention contemplates mounting the vestibular stimulation system on the user at a variety of locations and in a variety different ways. For example, instead of mounting the control unit on the arm via an armband, it can be mounted on the belt using a belt clip, on the head using a headband, on the torso using a torso strap, on the leg using a leg strap, and so on. A lanyard, strap, tether or other device can be used to at least loosely attach the control unit to the user.

In one embodiment, the control unit is mounted or housed in components that are provided at the patient's bedside. For example, the power supply and controller are provided in a housing that rests on a nightstand, and the components worn by the user include only the electrode assemblies that are disposed on, in, or near the ear. This embodiment is disadvantageous in that it requires some form of tether or hard-wired connection that connects the power supply provided at the patient's bedside to the electrode assembly worn by the user's head. In an exemplary embodiment of the present invention the control unit at the patient's bedside also includes features typically found in items located at a bedside, such as a clock, an alarm, a radio, a clock/radio, a compact disc player, an MP3 player, or any combination thereof, that the user may desire. In short, the vestibular stimulation system can be incorporated into an alarm clock/radio that is typically found on many user's nightstands.

It can be appreciated that many users may not want to be physically tethered to a bedside unit. Thus, the present invention contemplates providing the components of the vestibular stimulation system in a system that is worn entirely on the user in addition to the armband embodiment noted above. As described above, a wireless communication link can be provided to enable remote functions from a bed-side unit to control the system worn on the patient, such as a user control interface on a bed-side controller sending control signal to the patient worn system. The patient-worn controller can include, for example, a wrist mounted controller that sends signals to the bed-side and/or patient mounted components to control the vestibular stimulation system. Further embodiments of the present invention that are directed along these lines are discussed below.

Figure 6:
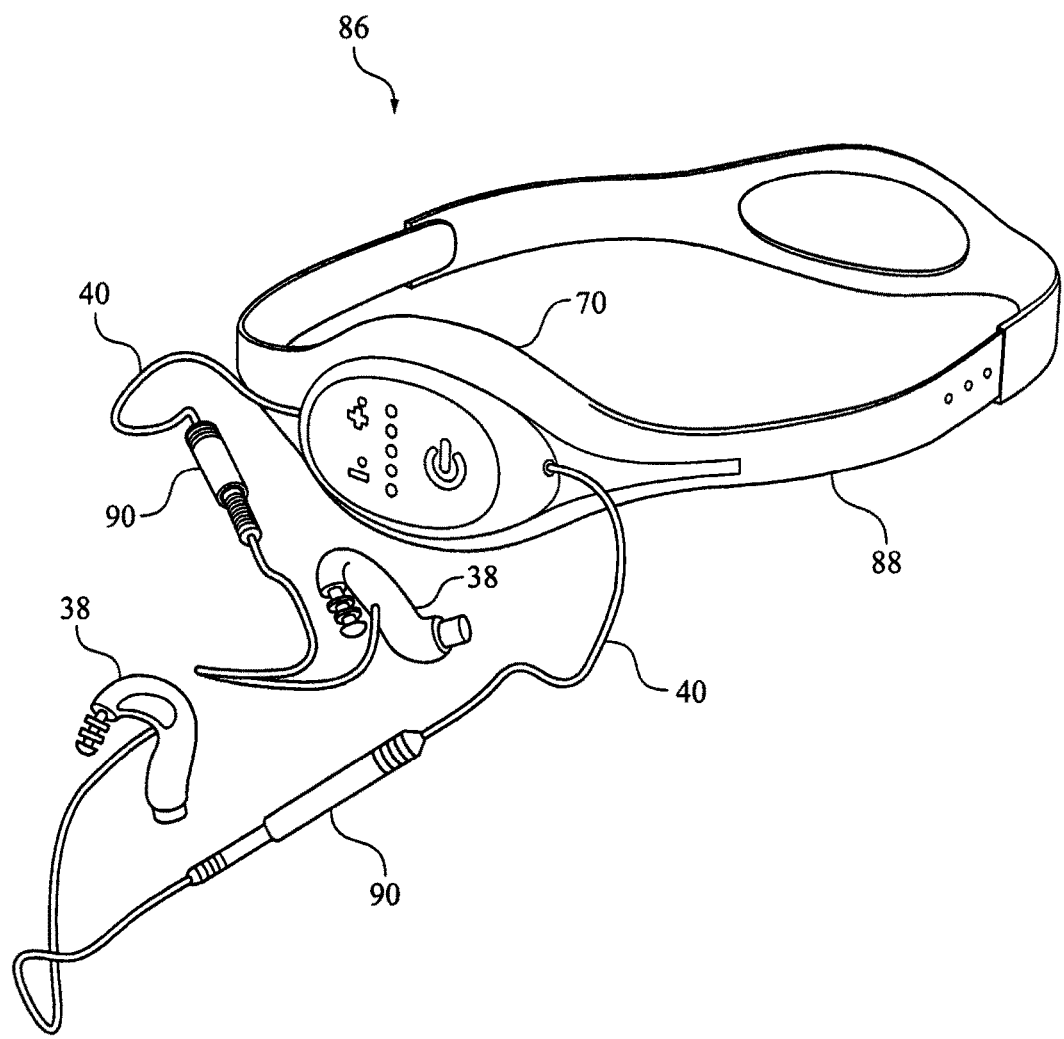
FIG. 6 is a perspective view of a headband assembly for supporting a vestibular stimulation system according to the principles of the present invention.
Figure 8:
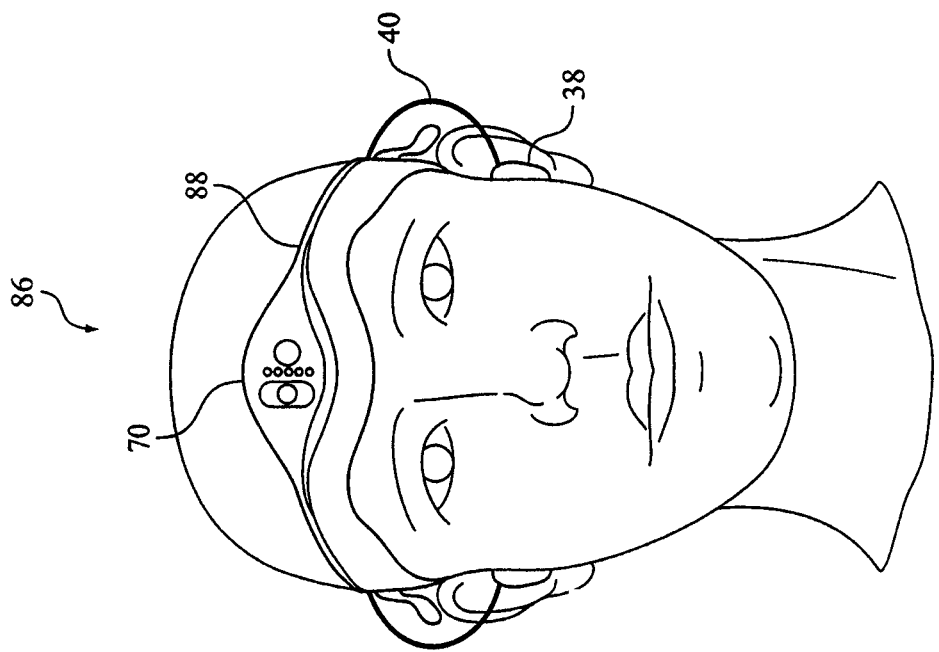
FIG. 8 is a front view showing the headband assembly of FIG. 6 being worn by a user.
Figure 7:
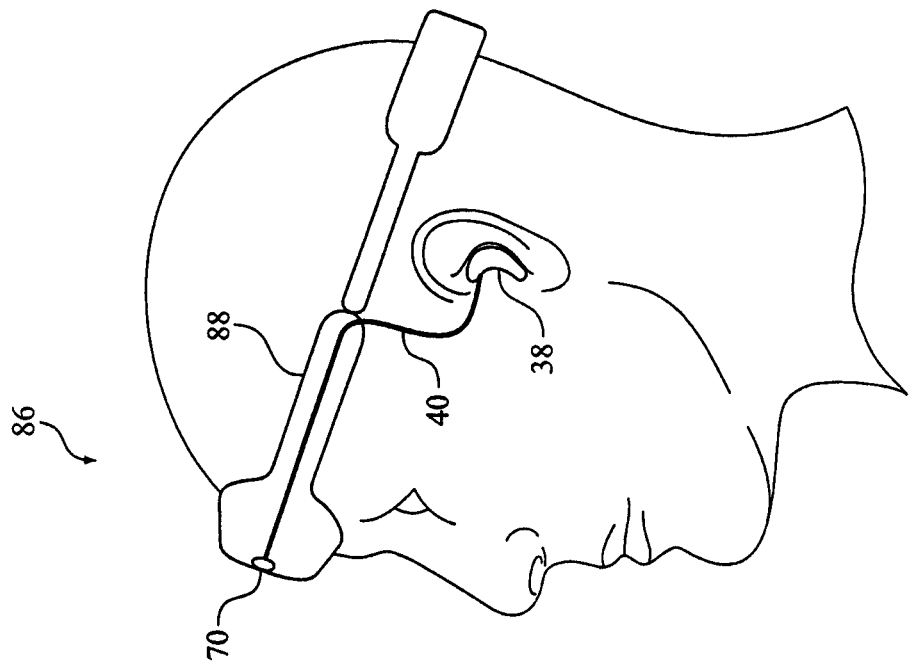
FIG. 7 is a side view showing the headband assembly of FIG. 6 being worn by a user.

FIGS. 6-8 illustrates an exemplary embodiment of a headband assembly 86 for mounting one or more components of vestibular stimulation system 30 directly on the user's head. Headband assembly 86 includes a headband 88 and control unit 70, which is either permanently or selectively attached to the headband. In the illustrated embodiment, the control unit a relatively small device that is mounted on the front of the headband. However, it can be mounted on other locations or the components can be mounted on various locations of headband 88. See, e.g., FIG. 22 discussed in detail below. The length of headband 88 can be adjustable using any conventional technique so as to fit a variety of different head sizes. In this illustrated exemplary embodiment, headband 88 is formed from two elements that are coupled together via one or two attachment elements. The amount of overlap between the two elements is adjustable to control the overall length of the headband. All or portions of headband 88 can be made from an elastic material to also provide ease of fitting and comfort. In addition, padding can be provided at any location along the headband to maximize patient comfort.

In the illustrated embodiment, electrical leads 40 extends from opposite sides of control unit 70. As shown in FIGS. 7 and 8, the electrical leads can be provided such that they follow or run along at least a portion of headband 88. A connection portion 90 selectively connects electrodes 38 to the control unit. For example, connection portion 90 can include mating male and female portions, one of which is associated with the electrical lead connected to the controller unit, the other of which is associated with the electrode. One advantage of this type of headgear assembly is that the electrodes are located in proximity to the control unit, thereby minimizing the length of the electrical leads. In the embodiment illustrated in FIGS. 6-8, electrodes 38 are "ear-bud" type electrodes, in which a portion of the electrical contacting structure is located in the user's ear canal. Such electrodes are described in detail in the '062 application.

The present also contemplates that the headgear used to support the control unit can also be used to support the electrodes in the desired position, such as behind the ear, on or near the mastoid. FIGS. 9-17 illustrate examples of this configuration. Holding electrical components in such a close proximity to the patient's ears avoids the need to provided a tethered link with the control unit or other components. Thus, the patient has the freedom to toss and turn while the device is being used without becoming entangled in the electrical leads, for example.

Figure 9:
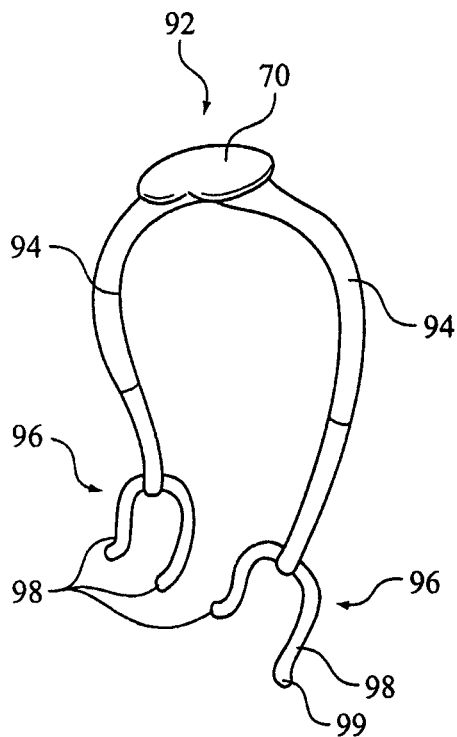
FIG. 9 is a perspective view of a further embodiment of a headband assembly for supporting a vestibular stimulation system according to the principles of the present invention.
Figure 10:
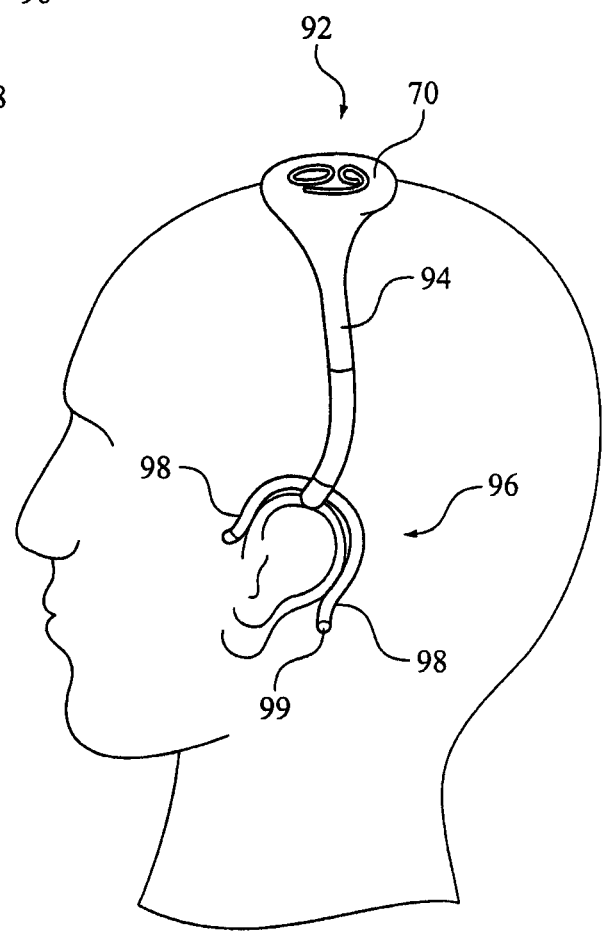
FIG. 10 is a side view showing the headband assembly of FIG. 9 being worn by a user.

FIGS. 9 and 10 illustrate a headgear assembly 92 that supports the vestibular stimulation system. In this embodiment, the headgear assembly includes a control unit 70 that is positioned on the top of the user's head. A pair of arms 94 extend from the control unit. In an exemplary embodiment, the aims are biased toward one another so that they provide a clamping force on the user's head, thereby securing headgear assembly 92 on the user. The length of the arms can be adjusted using any conventional technique so that the headgear assembly can be comfortably fit on a wide variety of users.

Electrodes assemblies 96 are mounted on the end of each arm. In this embodiment, the electrode assemblies are shaped to correspond, in general, to the shape of at least a portion of the human ear. That is, each electrode assembly includes a pair of wings 98 with an electrical conductor 99 mounted on one or both of the wings. The wings are configured in a horse-shoe or U-shape to facilitate positing the electrodes at the correct location on the user and/or to maintain the electrodes on the user. The electrode assemblies can be fixed to arms 94 or selectively connected to the arms. Wings 98 can be rigid, flexible, or semi-rigid. For example, the present invention contemplates that the wings are bendable, and maintain their shape once moved to a given position. The electrical leads are provided within arms 94 and within at least one wing 98.

Figure 11:
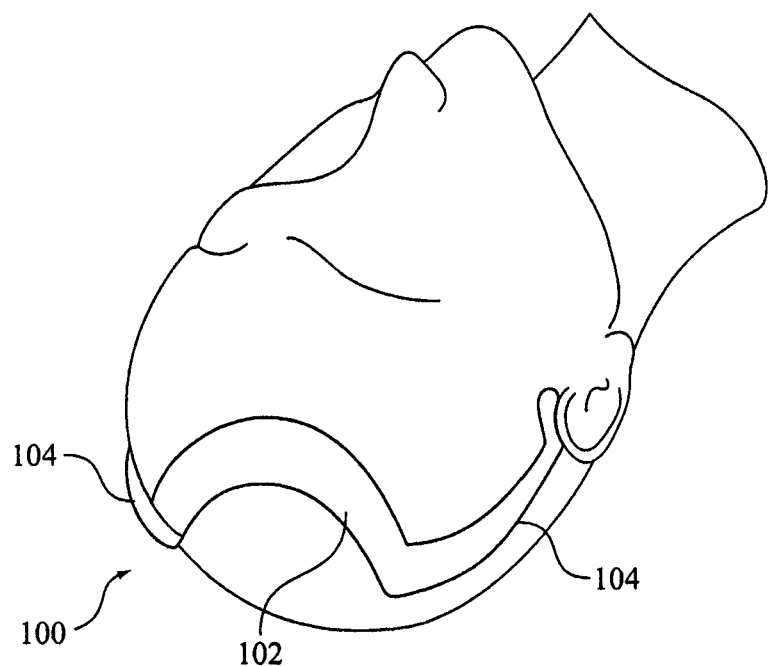
FIG. 11 is a top perspective view of a still further embodiment of a headband assembly being worn by a user.

FIG. 11 shows a head-mounted vestibular stimulation system that is a slight variation of the embodiment shown in FIGS. 9 and 10. In this embodiment, the components of the vestibular system are disbursed in a headgear assembly 100, rather than being grouped in a relatively bulk mass provided at one location. For example, in the illustrated embodiment, headgear assembly 100 includes a housing portion 102 that spans the top of the head and that is flatter than the control unit of the previous embodiment. The present invention contemplates arranging the electrical components on a flexible circuit board contained in housing portion 102 that is also made from a flexible material. This configuration enables the housing portion to contour to the patient's head for further comfort.

In the illustrated embodiment housing portion 102 is C-shaped, which helps it sit snugly on the top of the human head. The components typically found in the control unit, such as the power supply and the controller, are contained in the housing. The input/output interface (not shown) can be provided on housing portion 102. A pair of arms 104 extend from the housing portion, with the electrode assembly being mounted on the end of each arm. To vary the fit of the headgear assembly to match the head of the user, the length of the arms can be adjustable, the shape of housing portion 102 can changed, or both.

In a further embodiment, the headgear is made up of two halves of material with a sliding band used for adjustment. The electrical components are arranged on a flexible circuit board that has two extensions arranged in such a way that they have the ability to adjust to fit the patient's head based on the size determined by the sliding band. The electrical components residing on a flexible circuit board allow the entire device to match the contours of the user's head through the surrounding material enclosure. The two extensions are arranged inside a material enclosure so that the left extension wraps over the body of the board to the right and the right extension wraps over the body of the board to the left. The extensions of the circuit board terminate directly at the electrode. As the internal sliding mechanism is adjusted to fit the patient's head from ear to ear, the overall length of the flexible circuit board remains fixed.

Figure 12:
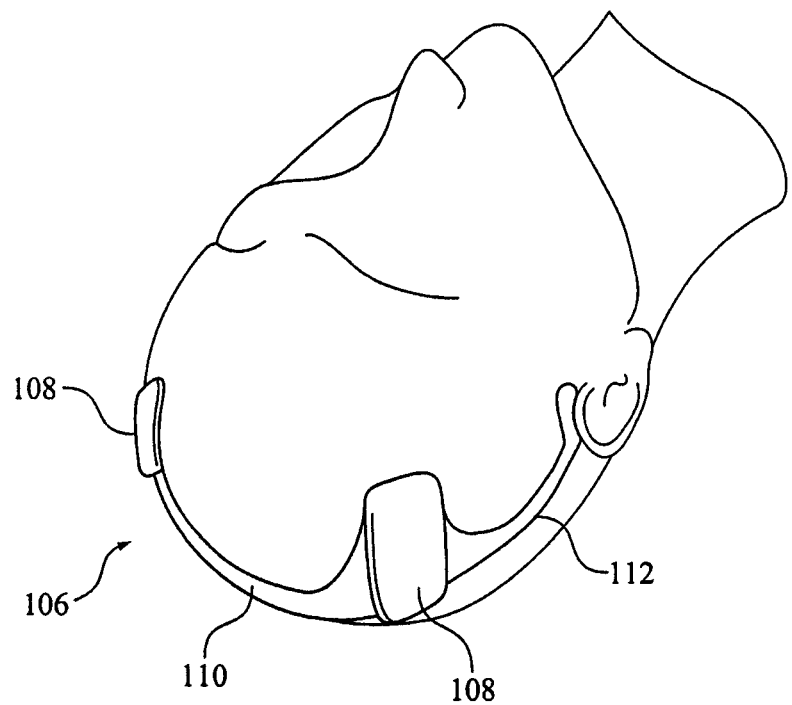
FIG. 12 is a top perspective view of a yet another embodiment of a headband assembly being worn by a user.

FIG. 12 illustrates a still further variation or a headgear assembly 106 that supports the vestibular stimulation system of the present invention. In this embodiment the components of the control unit are disbursed into a pair of pods or nodes 108 that are disposed on opposite sides of the centerline of the user. This configuration helps balance the weight of the system on the head of the user. A support member 110 couples the nodes and an arm 112 extends from each node to locate the electrode assembly on the user. The length of support member 110, arms 112, or any combination thereof can be adjustable so that headgear assembly 106 can be fit to a variety of differently sized individuals.

Figure 13:
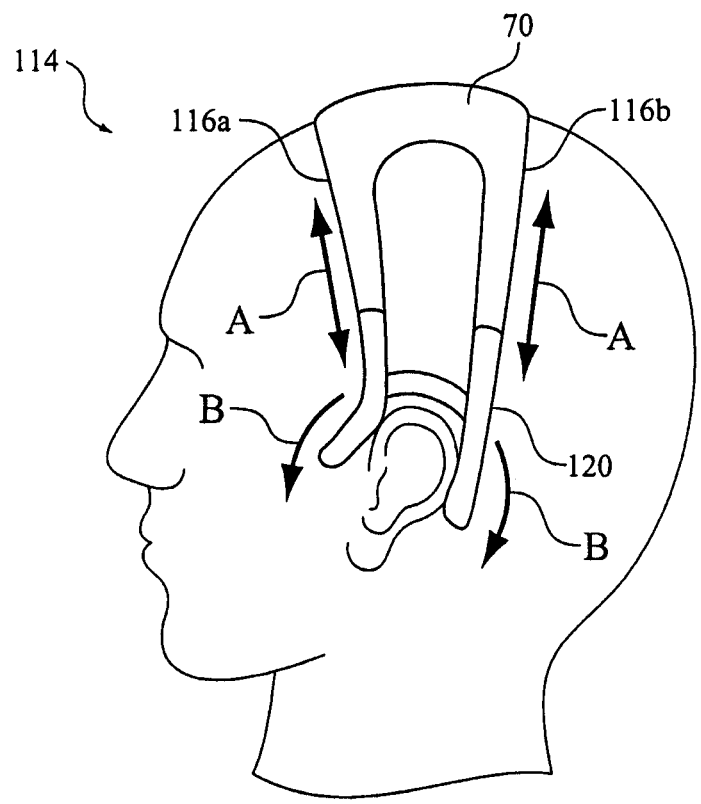
FIG. 13 is a side view showing a headband assembly according to another embodiment of the present invention being worn by a user.
Figure 14:
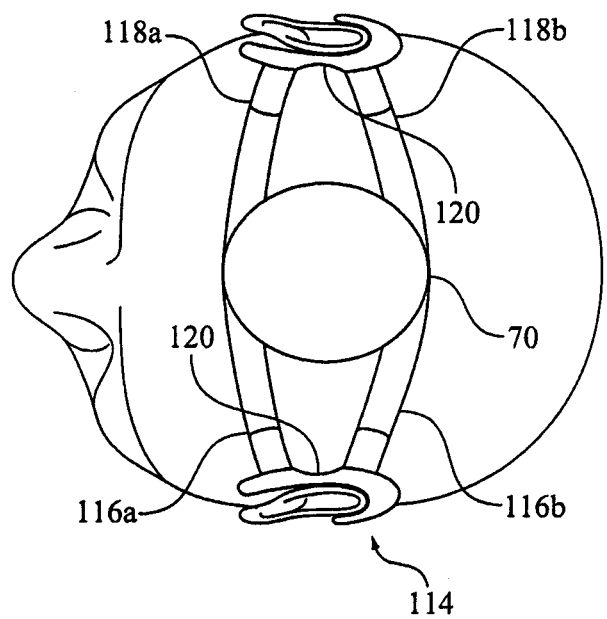
FIG. 14 is a top view of the headband assembly of FIG. 13 being worn by a user.

FIGS. 13 and 14 illustrate a headgear assembly 114 according to a further embodiment of the present invention. A control unit 70 is mounted at a central portion of the headgear assembly. A pair of arms 116a, 116b and 118a, 118b extend from each side of the control unit. As indicated by arrows A, the length of the arms are adjustable. In addition, as indicated by arrows B, the arms 116a and 116b can be moved toward or away from each other to control the position of the electrode assembly on the user. The free ends of the arms are configured to fit around the ear of the user. A connecting member 120 couples the free end of the arms. In an exemplary embodiment, connecting member 120 is a flexible member. An electrical conductor is provided on at least one of the arms to provide the vestibular stimulation to the user. Again, the electrical leads that couple the conductor to the control unit can be buried within the arms.

Figure 15:
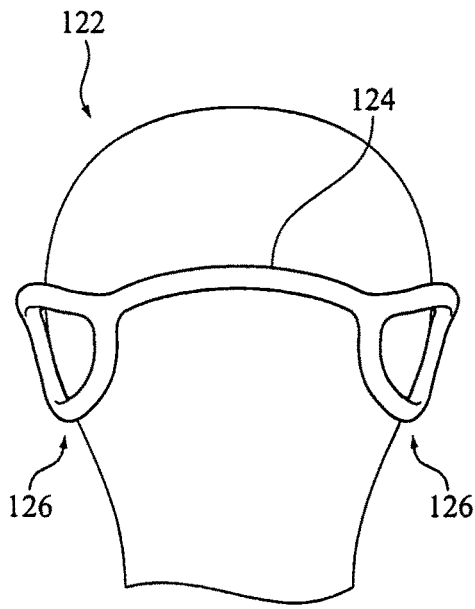
FIG. 15 is a back view of a headband assembly according a further embodiment of the present invention being worn by a user.
Figure 16:
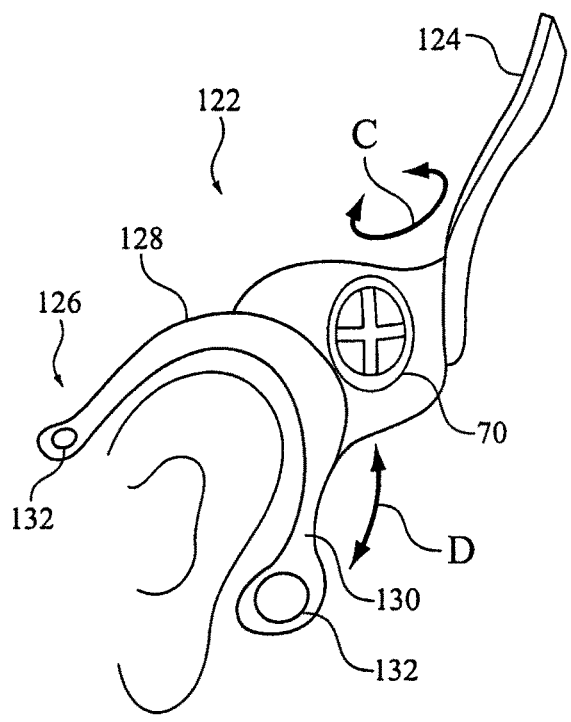
FIG. 16 is a side view of a portion of the headband assembly shown in FIG. 15.

FIGS. 15 and 16 illustrate a headgear assembly 122 in which at least one support 124 spans the back of the user's head. A control unit 70 is coupled to at least one end of support 124 and an electrode assembly 126 is coupled to the control unit. In an exemplary embodiment, the control unit is moveably or rotatably connected to support 124, as indicated by arrow C. In addition, electrode assembly 126 moveably or slidably connected to control unit, as indicated by arrow D.

Electrode assembly 126 includes a pair of wings or arms 128 and 130, with a conductor 132 coupled to at least one of the wings. Arm 128, 130, or both are formed from a rigid material, a semi-rigid material, a formable material (a material that retains the shape once moved to a new shape), or a flexible material. It should be noted that all of the components of the vestibular stimulation system can be provided on one control unit provided at one end of support 124. The present invention also contemplates that the components of the vestibular stimulation system can be distributed at each side of the patient, i.e., at each end of support 124.

Figure 17:
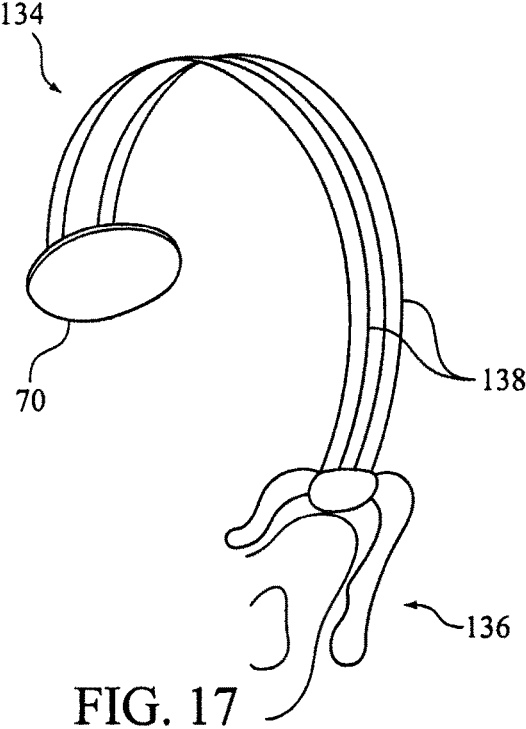
FIG. 17 is a front perspective view of an asymmetrical headband assembly for supporting a vestibular stimulation system on a user according to the principles of the present invention.

In the previous embodiments, the headgear assembly has a generally symmetrical configuration so that an electrode assembly is supported by the headgear assembly on both the left and right side of the user. It is to be understood that the present invention contemplates that the headgear assembly can be configured so as to locate the electrode assembly on only one side of the user, i.e., asymmetrical. FIG. 17 illustrates an exemplary headgear assembly 134 having such a configuration. In this embodiment, control unit 70 is located on one side of the user and an electrode assembly 136 is provided on another side of the user. A support or pair of supports 138 connect the control unit to the electrode assembly.

Figure 18:
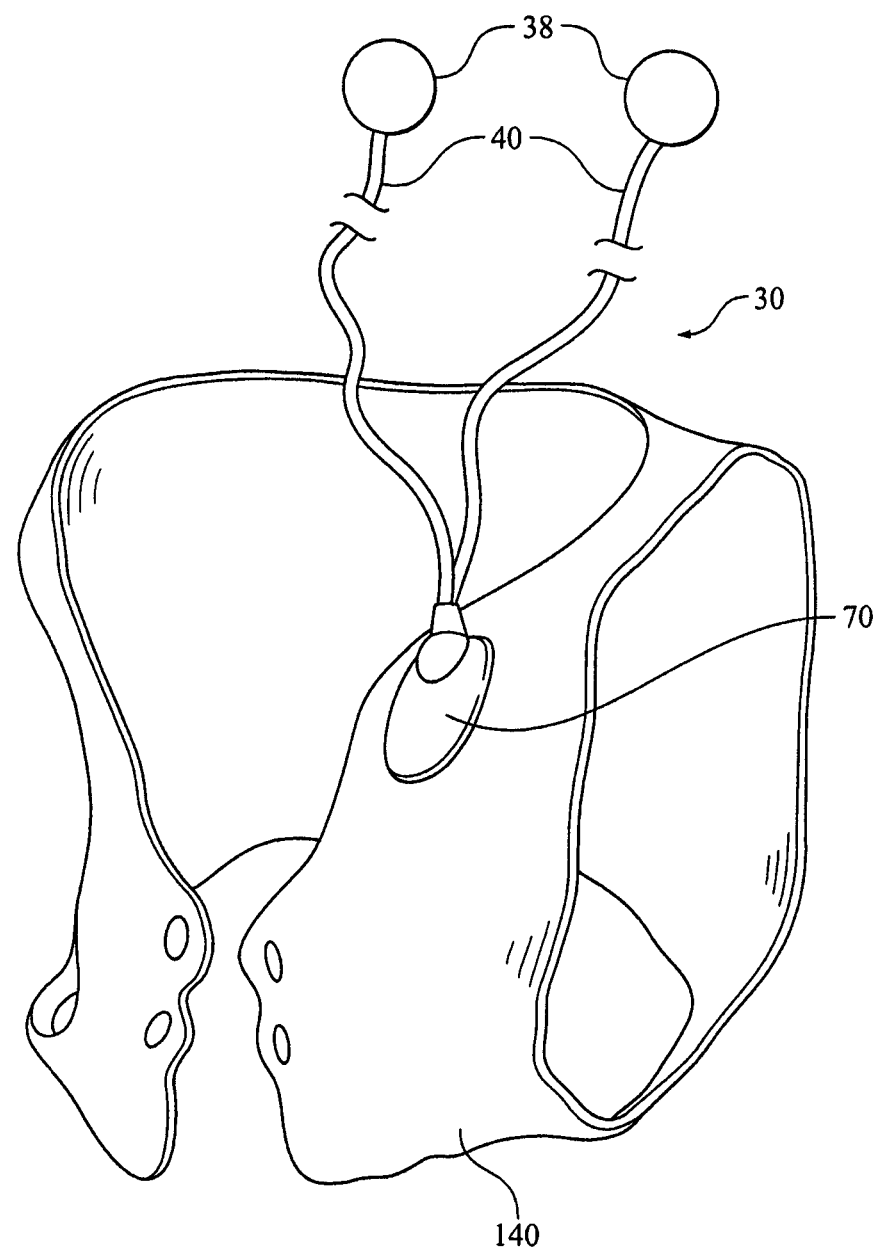
FIG. 18 is a perspective view of a vest for supporting a vestibular stimulation system on a user according to the principles of the present invention.
Figure 19:
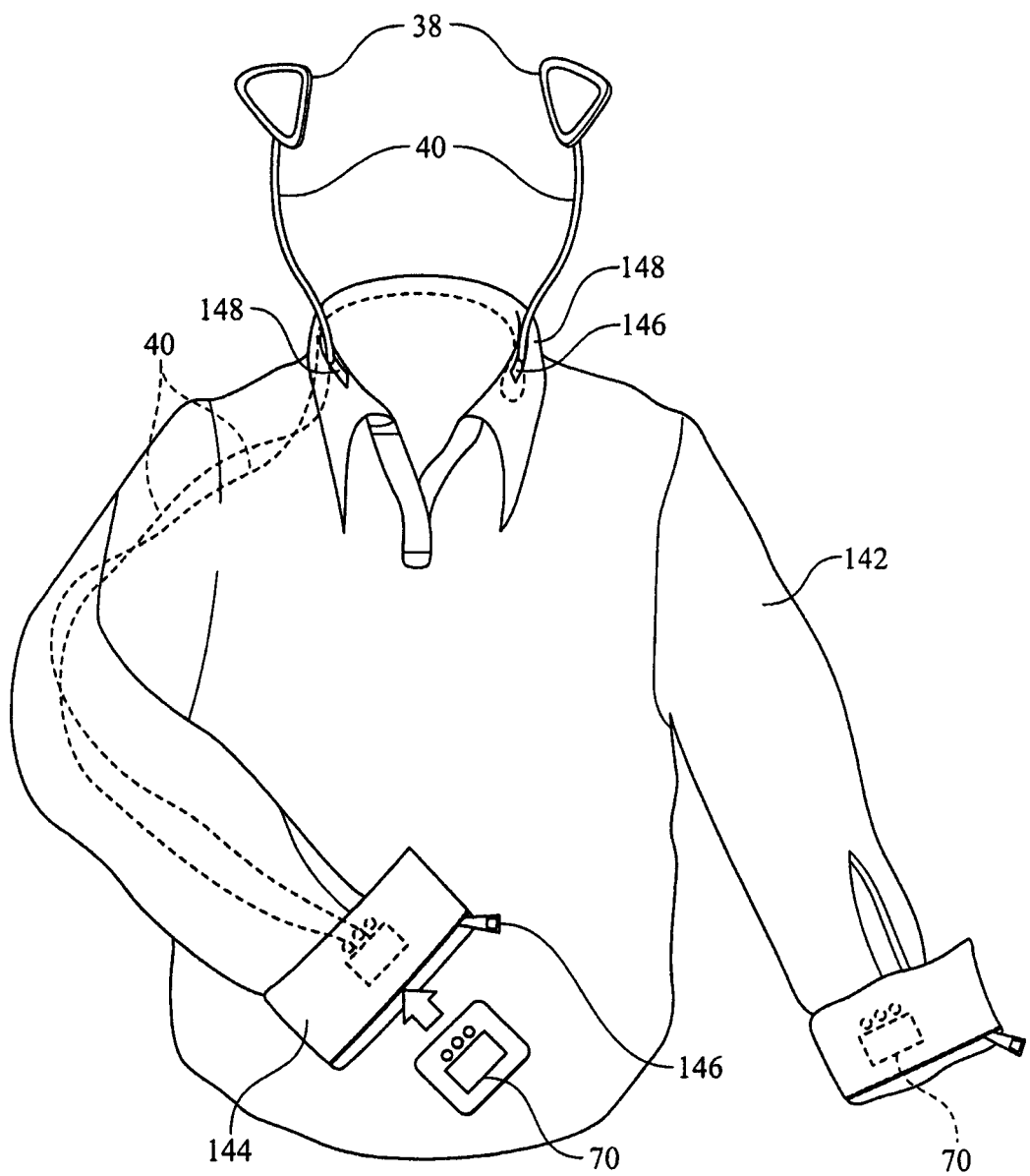
FIG. 19 is perspective view of a garment adapted to support a vestibular stimulation system on a user according to the principles of the present invention.

As noted above, the present invention contemplates that the electrical components of the vestibular stimulation system can be mounted on the user in a variety of ways. FIGS. 18 and 19 illustrates mounting the vestibular stimulation system via a garment worn by the user. More specifically, FIG. 18 illustrates a vest 140 that supports a vestibular stimulation system 30 according to the principles of the present invention. In this embodiment, control unit 70 is mounted directly on vest 140 using any suitable attaching mechanism. For example, control unit 70 can be permanently sewn, adhered, bonded, or mechanically coupled to the vest. The control unit can also be removably coupled to the vest, for example by providing a pocket for containing the control unit or selectively clamping or strapping the control unit to the vest.

FIG. 19 illustrates a garment 142, such as a nightshirt, pajama top, or other sleep ware, that is worn by the user and that support the vestibular stimulation system of the present invention on the user. The embodiment demonstrates that one or more components of the vestibular stimulation system, such as controller 70, can be housed or concealed in a pocket provided in the garment. In this embodiment, for example, a pocket is provided at the end of a sleeve 144. Access to the pocket is gained or denied via a zipper 146 so that the pocket can house the control unit. In the illustrated embodiment, pockets are provided at the end each sleeve so that the user can select which pocket to use.

Electrical leads 40 are disposed in the garment, for example, stitched to the fabric, and run from the pocket to a collar portion 146. Slots or openings 148 are provided in the collar portion to provide access to the electrical leads for connection to electrodes 38. It is to be understood that the location of the pocket or pockets can be varied. In addition, the type of garment in not limited to those shown in the figures. For example, the present invention contemplates that the vestibular stimulation system of the present invention can be attached to a night cap, pajama bottom, or any other garment worn by the user.

Figure 20:
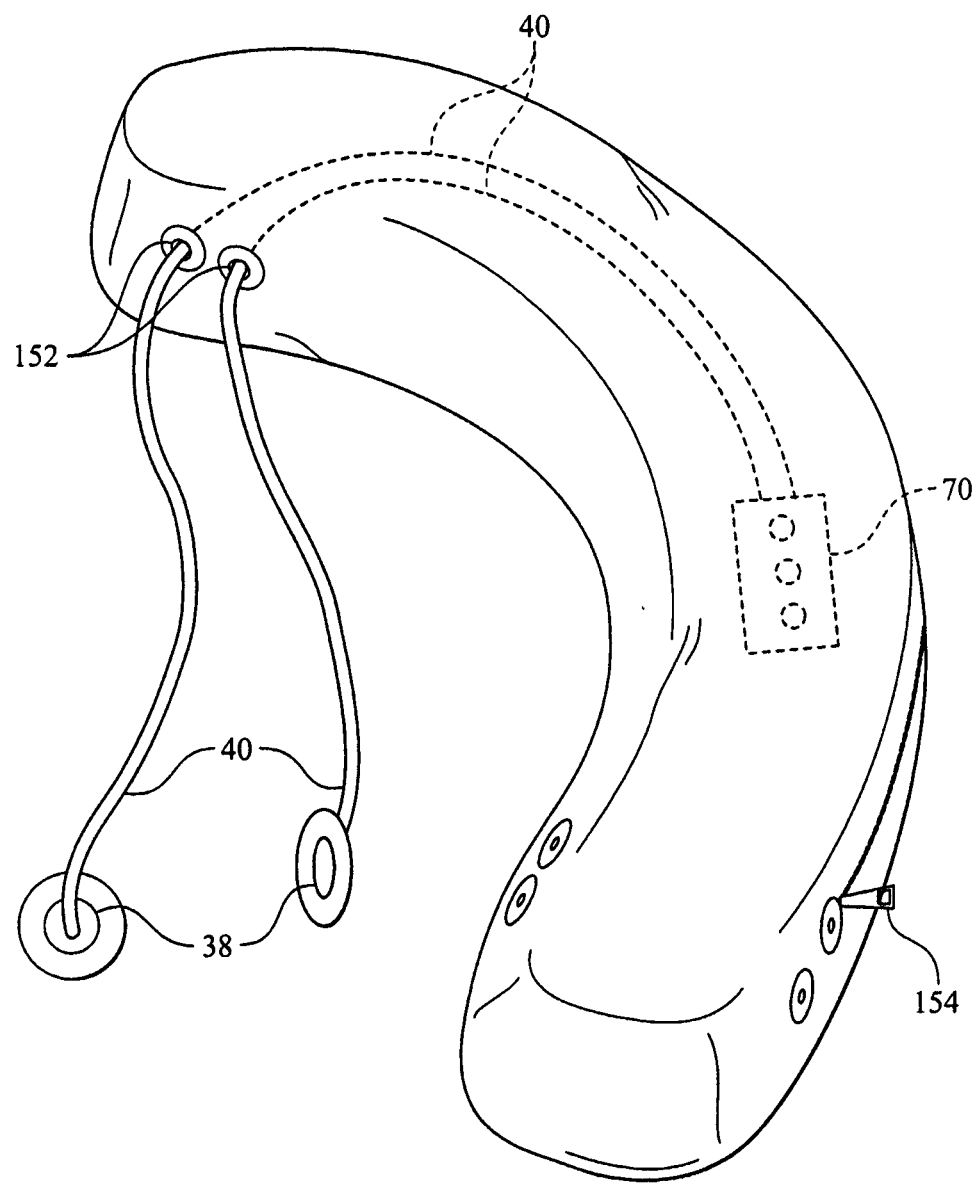
FIG. 20 is a perspective view of a pillow adapted to contain at least a portion of a vestibular stimulation system on a user according to the principles of the present invention.

In the embodiments described thus far, the vestibular stimulation system is worn on the user. The present invention also contemplates providing one or more components of the system at a location near the user, but not directly attached to the user. For example, the power source and the controller can be provided in a pillow, sheets, bedding, or other element or apparatus that is normally disposed near the user during sleep. FIG. 20 illustrates an example of a pillow 150 according to such an embodiment.

In the illustrated exemplary embodiment, pillow 150 includes a recess, cavity, or pocket for retaining an concealing control unit 70. Electrical leads 40 are imbedded within the pillow and exit via openings 152 for coupling to electrodes 38. A zipper 154 is provided for accessing the cavity in which the control unit is located. The present invention further contemplates providing ventilation ports for allowing ambient air to reach the control unit so as to minimizing overheating of the control unit.

The pillow can have a variety of different sizes, shapes, and configurations. For example, a conventional rectangular pillow can be used to house the control unit. The pillow can also be made from a variety of materials or combination of materials, such as foam, feathers, or any other conventional material. Of course, the pillow can include other features found in pillows, such as massaging or vibrating devices, heating or cooling devices, sound generators, radios, and so on. The present invention further contemplates that the pillow can be worn on the user, for example, by strapping the pillow around the head and/or next. In which case, the pillow is effectively a garment worn by the user.

Figure 21:
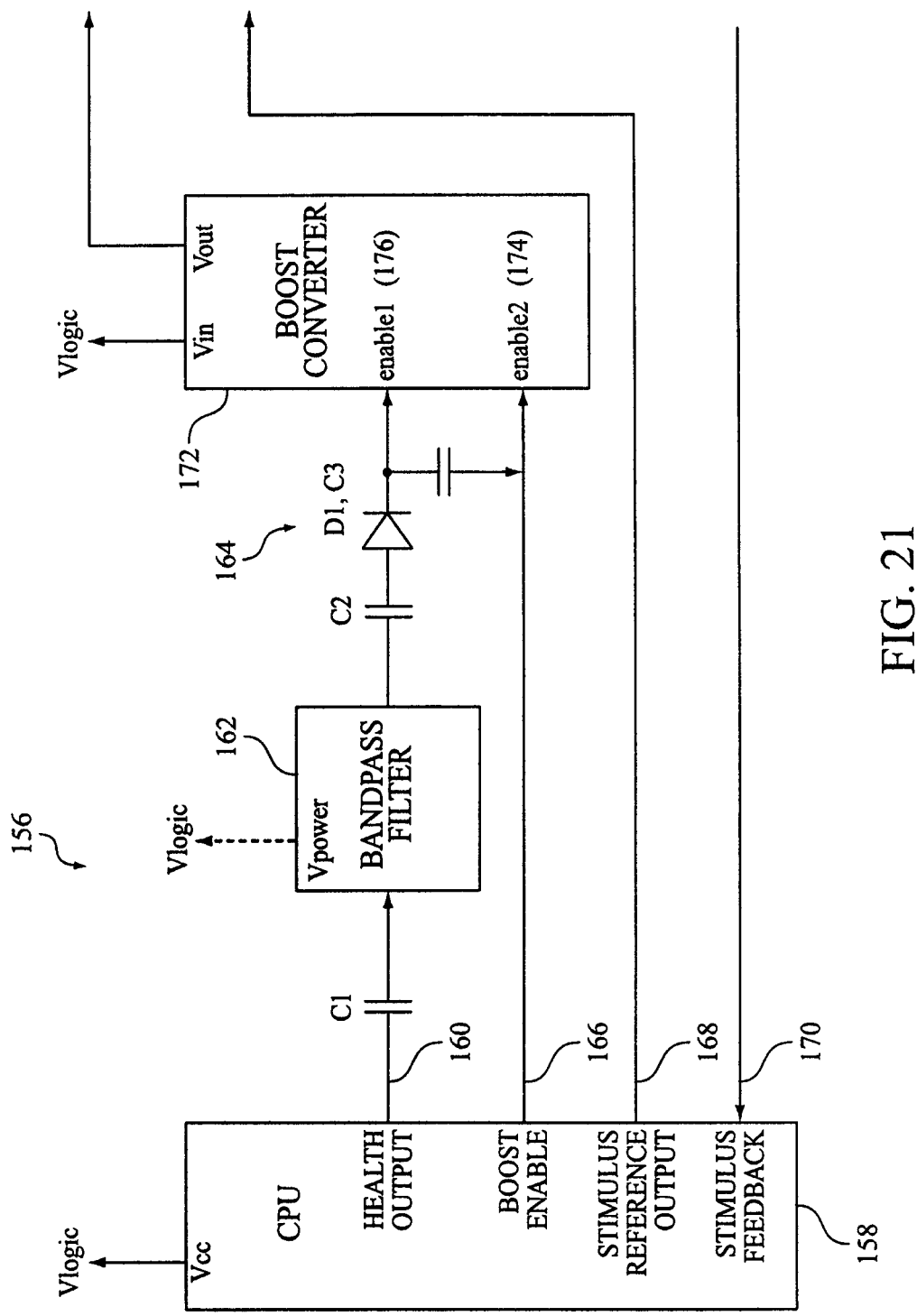
FIG. 21 is a schematic view of a stimulation circuit used to deliver a vestibular stimulation therapy according to the principles of the present invention.

The present invention contemplates using a "fail-safe" electrical circuit for providing the stimulation energy to the electrodes. Hardware or software current/voltage control techniques that are "fail-safe" ensure that the desired stimulation is output to the user, operates in a safe manner under normal circumstances, and ensures that a failure of any component or software functionality will not cause an unsafe output. FIG. 21 illustrates an exemplary embodiment of a "fail-safe" electrical stimulation control circuit 156 that is used to deliver stimulation energy the user. Thus, circuit constitutes one variation for controller 34 discussed above. It should be noted that the present invention contemplates that fail-safe electrical stimulation control circuit 156 can be used in other types of electrical stimulation devices, such as defibrillators and TENS devices, as well as the vestibular stimulation system of the present invention.

As shown in FIG. 21, fail safe stimulation control circuit 156 includes a processor 158 that executes a conventional fail-safe technique. For example, it is known to use some form of a watch-dog timer that halts the execution of the operating system software if a countdown timer is not reset or kicked in a prescribed time period. In an exemplary embodiment, processor 158 requires that the watch-dog timer kicks occur at a fixed rate, and also causes a digital output labeled "Health Output" 162 to toggle. The Health Output signal 160 is sent to bandpass filter 162 and demodulator circuit 164 that generates the energy necessary enable to stimulators output power source.

Processor 158 is responsible for the generation of a Stimulus Reference Output 168, a Boost Enable Output 166, as well as Health Output 160. In an exemplary embodiment, these output signals are digital signals. Stimulus Reference Output 168 is an internal signal that is amplified or otherwise conditioned before it is applied to the patient or actuator device. A Stimulus Feedback signal 170 is provided to processor 158. The processor uses this signal to verify that the device is or is not delivering output power. A boost converter 172 steps-up a Vlogic supply voltage from the usual range of 3-5 VDC to something greater. The specific increase provided by boost converter 172 will depending on the stimulation to be provided to the user. For example, a TENS device may use a 12 VDC boost voltage, whereas a defibrillator require a voltage greater than 1000 VDC.

Boost Enable Output 166 is used to enable or disable boost converter 172 via software based on the signal present at enable2 input 174. This control line works independent of the "fail-safe" enable and allows the processor to control the output power. Health Output is a discrete digital output that is toggled each time the operating system software completes a specific set of tasks that verify its own health and a RESET supervisory timer has been kicked. If the cycle time of the operating software is consistent and predictable, the Health Output is a very regular square wave at a frequency equal to the reciprocal of the cycle time.

The Health Output square wave is coupled to bandpass filter 162 by a DC blocking capacitor C1. The bandpass filter has a very sharp response at the operating system software's cycle time. The bandpass filter can be implemented using discrete passive components, an active implementation using operational amplifiers, a crystal or naturally resonant device, and/or any frequency dependent devices. Capacitor C2 is used to block DC that may come from the bandpass filter. Diode D1 and capacitor C3 are used to rectify and filter the AC output from the bandpass filter. The rectified voltage is applied to the boost converter's enable1 input 176, which allows the boost converter to produce an output voltage that is used by an output amplifier or similar output device.

The operating system software architecture must be designed so that Health Output signal 160 is only capable of toggling at the bandpass filter frequency when the critical routines have executed properly. This constraint fits well with most state machine and watch-dog timer guarded embedded systems. This implementation inherently traps changes in the system's master timebase. Processor 158 can also execute a built in self test (BPST) routine that tests discrete combinations of the CPU's Boost Enable Output 166 and Health Output 160 against Stimulus Feedback signal 170 to verify that bandpass filter 162, demodulator 164, and boost converter 172 operate as expected. The implementation results in controllable, "fail-safe", voltage source that can be used to deliver power to a stimulator's output stage, an actuator, or critical sensor.

Several advantages of fail safe stimulation control circuit 156 over conventional fail safe techniques are as follows:

1) The "fail-safe" validation process is simplified because it places a single constraint on power output delivery. Failure analysis and injection can be tested against their impact of the frequency of the health output.

2) Stimulation control circuit 156 eliminates the need for a second timebase and the associated crosscheck in timing sensitive applications.

3) Stimulation control circuit 156 can be used to deliver and control power in critical applications that require zero detection latency where the output is never permitted to be out of range, i.e., heart and brain stimulators.

Conventional "fail-safe" power supply designs use closed loop architectures that verify the integrity of the output signal via feedback paths. These devices can only detect out of range conditions, which must occur for a finite amount of time before the output is disabled. Other devices limit their output capability under all conditions via electronic fuses, limit the primary power source, or controlled impedance paths. Fail-safe stimulation control circuit 156 of the present invention stops delivering output power when the software system fails to operate as expected. It does not require an out of range output condition to detect a failed component or software operation.

Figure 22:
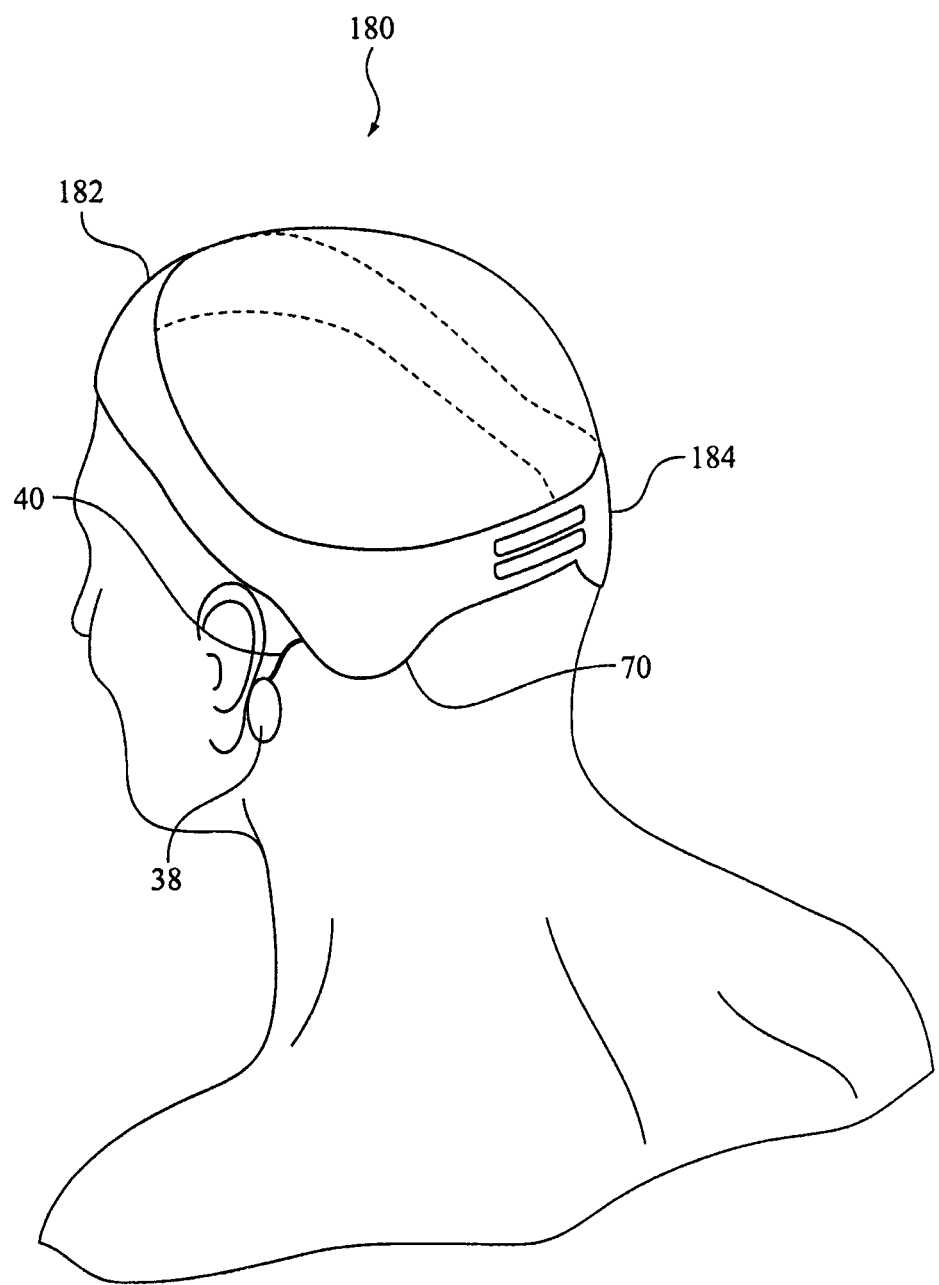
FIG. 22 is a perspective view of a headband assembly for mounting one or more components of vestibular stimulation system directly on the user's head.

FIG. 22 illustrates an exemplary embodiment of a headband assembly 180 for mounting one or more components of vestibular stimulation system 30 directly on the user's head. Electrical leads 40 extending from control unit 70 communicate signals between the control unit and electrodes 38 disposed on the user. It should be noted that only one electrical lead 40 and electrode 38 is shown in FIG. 22. In practice, a second electrode would be located elsewhere on the user, such as proximate to the vestibular system on the other side of the user. One advantage of this type of headgear assembly is that the electrodes are located in proximity to the control unit, thereby minimizing the length of the electrical leads.

Headband assembly 180 is functionally similar to headband assembly 86 of FIGS. 6-8. Headband assembly 180 includes a headband 182 and control unit 70, which is either permanently or selectively attached to the headband. In the illustrated embodiment, the control unit a relatively small device that is mounted on the rear of the headband. A power supply 184 is provided on headband 182 in a symmetrical location with respect to control unit 70 so that the weight of the power supply and the control unit are balanced on the headband assembly. Of course, the present invention contemplates that the components of the power supply and the control unit can be mixed so that portions of each are provide on each side of the headband assembly, rather than in discrete modules, as shown.

The length of headband 182 can be adjustable using any conventional technique so as to fit a variety of different head sizes. All or portions of headband 88 can be made from an elastic material to also provide ease of fitting and comfort. In addition, padding can be provided at any location along the headband to maximize patient comfort. It is believed that mounting the heavier, bulkier components of the vestibular stimulation system behind the head, preferably near the interface between the skull and the top of the neck, provides a comfortable way of mounting the device on the head that most users can tolerate for extended periods of time.

II. Stimulation Control

A. Stimulation Activation and/or Deactivation

The present invention contemplates that the stimulation energy is provided by the control unit only if the stimulation system is properly connected configured, i.e., all of the components of the device are connected properly and the components are deemed to be functioning properly. Thus, any electrical disconnections of the electrical leads are detected, for example by performing diagnostic operations. The stimulation energy is not provided if a fault condition exists. A warning can be provided to the user to alert them of the fault condition.

In a further embodiment, the stimulation energy is provided only if the electrode assemblies are properly positioned on the user. There are a variety of techniques that can be used to determine whether the electrodes are properly positioned on the user. In one embodiment, the resistance between two or more electrodes needed to provide the stimulation therapy can be measured. If the electrodes are properly positioned on a human head, the head resistance should be within an identifiable range. If the measured resistance does not fall within the predetermined range or above or below a predetermined threshold, the system can be prevented from administering the stimulation therapy and a fault condition can be indicated. For example, the user can be prompted (visually or audibly) to reattach the electrodes on the skin.

The present invention further contemplates controlling the application of the stimulation therapy based on the location of the user relative to his or her sleep apparatus, for example, whether the user is actually in his or her bed. For purposes of this invention, the sleep apparatus is any device where the user sleeps, such as a bed, chair, hammock, couch, etc. It can be assumed, for example, that if the user is in their sleep apparatus, they are attempting to fall asleep. In which case, the stimulation therapy is delivered. If they are not in their sleep apparatus, the stimulation therapy is discontinued. A location monitoring assembly is used to monitor whether the patient is at his or her sleep location.

The present invention contemplates using one or more of the numerous devices and techniques for determining whether a user is at a particular location, i.e., at or in the sleep apparatus. For example, one or more sensors, such as pressure, sound, or temperature sensors can be arranged on, in, or near the sleep apparatus to detect the presence of the user in the sleep apparatus. Such sensors can also be provided in the bedding accessories, such as the pillows, sheets, and blankets. In addition, one or more sensors can be deployed at a location remote from the user to detect the location of the user. For example, thermal imaging, infrared detectors, motion sensors, and the like can be used to determine whether the user is in the sleep apparatus.

In addition, a tether (hardwired or wireless) can be coupled to the user so that as long as the user is within the boundary or range given by the length of the tether, the user is assumed to be in the sleep apparatus. An example of a wireless tether is a radio frequency device, RFID device, IR device or any other electronic device that is detected by a home station. The home station can monitor the position of the electric either in an actual or area or relative to the home station. If this position indicates that the user out of the sleep apparatus, a signal can be provided to the vestibular stimulation system that causes it to discontinue the stimulation therapy.

The inventors recognized that blood flow and blood pressure change with position of the user, the sleep stage of the user, or both. These changes affect the resistance of the skin. This resistance can be measured by monitoring the voltage applied across one or more pairs of stimulation electrodes and the current through the skin as the stimulation therapy is being applied. In an exemplary embodiment of the present invention, when therapy is initiated, an initial resistance measurement is recorded as the benchmark resistance of the initial sleep position. The skin resistance is measured at each peak of the therapy sine wave throughout the therapy session or during the therapy window. This dynamic resistance measurement is compared to the benchmark resistance. If the patient leaves the sleep position, his blood pressure and blood flow will increase dropping the skin resistance. If this change in resistance is beyond a predetermined threshold, it can be concluded that the user has changed is position or sleep state, so that the stimulation therapy should be discontinued or otherwise altered.

Of course, a probe signal can be generated by the device that is different than the therapy signal for the purpose of measuring various characteristics of impedance electrode-to-electrode. For instance, signals in the 100+ kilohertz range have been used to monitor the expansion of the chest. Similar frequencies may be used to monitor the user for sinus expansion or pulse. These probe signals can be used when therapy is not being delivered or by mixing them with the therapy signal.

This same dynamic skin resistance measurement technique can also be used to activate the stimulation therapy. Of course, periodic skin resistance measurements must be taken to assess whether the user entered a position and/or sleep state in which the therapy is to be delivered.

The present invention also contemplates monitoring heart rate/pulse rate using any conventional technique and controlling the stimulation therapy based on this monitoring. For example, the electrodes applied to the user can detect heart/pulse beats. The stimulation therapy can, for example, be activated when beats are detected and deactivated when not detected.

In one exemplary embodiment, vestibular stimulation system 30, upon activation, delivers initial and subsequent stimulation therapy for a predetermined period of time, such as 30 minutes to 8 hours. This period of time can be set in advance, programmed by the user, or set in any conventional way. The therapy is initiated by the user actuating therapy on button 54. The initial therapy is delivered while the user is in a sleeping position (prone or sitting) with the therapy electrodes properly connected. The initial therapy would be delivered for the predetermined period of time, e.g., 30 minutes, and then stop.

In an exemplary embodiment, the vestibular stimulation system detects sleep via a significant increase in skin resistance due to the drop in blood flow and/or blood pressure. The vestibular stimulation system replaces the skin resistance benchmark with higher values as the patient enters deeper sleep stages. A drop in skin resistance (but not low enough to indicate the patient has left their sleeping position) would then automatically restart the therapy for another set period of time, such as 30 minutes (or progressively less time as the therapy window progresses) if the therapy window hasn't expired. The therapy window is a period of time during which stimulation can be provided once the vestibular stimulation system is turned on. A typical time period for such a window is 6-12 hours. However, this window can be set or changed depending on the amount of time a user prefers to sleep. If the therapy window expires, the user removes the therapy electrodes, or the user rises (significant drop in skin resistance), the therapy will stop and the therapy window will close.

The present invention contemplates using a sensing technique that can safely disable the therapy when a user has left their sleep position and/or sleep apparatus. In a relatively simplistic embodiment, this functionality is achieved using a static tilt switch that senses when a user sat upright. This simplistic approach, however, requires that the tilt switch, such as a mercury switch or ball-bearing switch, be provided at a specific location on the user. In addition, the user needs to be in a near horizontal position to receive therapy.

In a more sophisticated embodiment, a multi-axis accelerometer is used at a wake/activity monitor to monitor the user's activity level and discriminate between a user who is repositioning himself or herself while remaining in his/her sleeping apparatus versus a user who is leaving their sleep position/apparatus. This allows the user to sleep in any position. The therapy is disabled if the user leaves their sleep position, and tolerates movements associated with changes in sleep position.

In more detailed embodiment the wake/activity monitor is based on a two-axis analog MEMS accelerometer that measures relative changes in tilt and vibration. In an exemplary embodiment, the accelerometer is implemented using fail-safe embedded techniques. In an exemplary embodiment, the two-axis analog MEMS accelerometer is the ADXL311 MEMS two axis accelerometer provided by Analog Devices. The ADXL311 is a low cost, low power, dual axis accelerometer with signal conditioned voltage outputs on a single monolithic IC. The ADXL311 will measure acceleration with a full-scale range of ±2 g, and measures both dynamic acceleration (e.g. vibration) and static acceleration (e.g. gravity). It provides two analog outputs that are proportional to the acceleration in two orthogonal directions. The typical noise floor for this sensor is 300 ug per root Hz at 3V operation, allowing signals below 2 mg (0.1° of inclination) to be resolved in tilt sensing applications using narrow bandwidths (10 Hz). The ADXL311 is available in 5 mm×5 mm×2 mm 8 lead hermetic LCC package.

In the present invention, the accelerometer is disposed in on the user, such as in housing 42. The signals provided by the accelerometer are provided to controller 34, that uses software to determine the roll and pitch angles of the housing relative to the earth's static gravitational acceleration. In an exemplary embodiment, the software uses vibration magnitude and change in tilt measurements on the two accelerometer channels/signals to determine if a therapy user is awake and active. If the user is active for a brief of period of time, therapy is interrupted and is continued when the activity has ceased. The therapy is stopped when the user's activity continues for an extended period of time.

Figure 24:
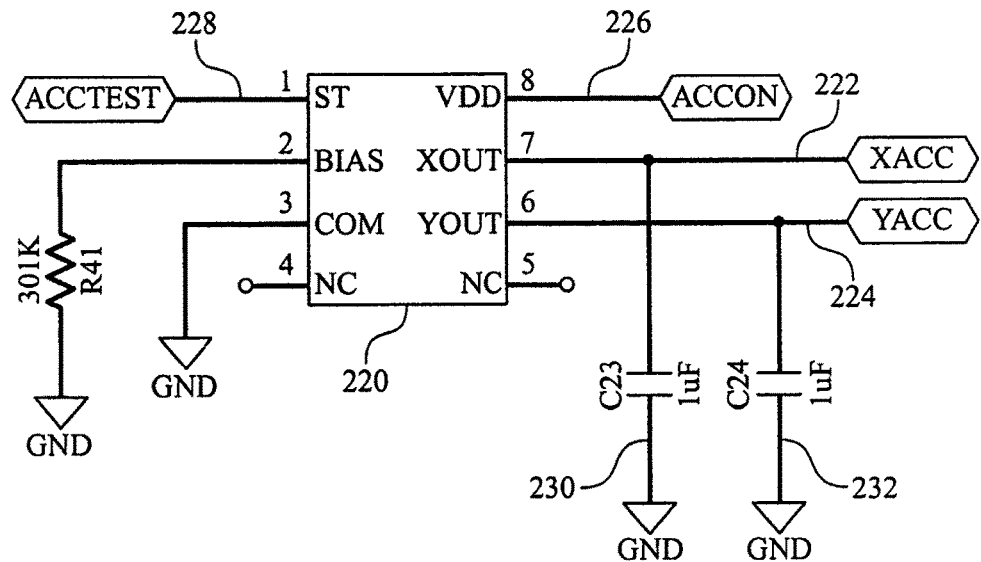
FIG. 24 is a schematic diagram of an accelerometer suitable for use in the vestibular stimulation system according to the principles of the present invention.

In an exemplary embodiment of the present invention, the accelerometer interfaces with a controller, such as a Texas Instruments MSP430 microcontroller. The MSP430 contains an analog-to-digital converter, 8-channel multiplexer, programmable references, and a flexible control interface. As shown in FIG. 24, accelerometer 220 includes analog outputs 222 and 224, which interface with to two of the controller. accelerometer 220 also includes a power on input 226 and a self test input 228, both of which interface with the controller. In an exemplary embodiment, the XOUT output 222 and YOUT output 224 are filtered with a pair of capacitors 230 and 232 that limit the frequency response. The values of capacitors 230 and 232 range from 0.01 uF to 0.47 uF for a respective upper frequency limit of 500 Hz to 10 Hz.

As noted above, controller 34, for example, uses accelerometer 220 to measure a therapy user's activity level and determine if therapy should be interrupted. The accelerometer's X and Y axis channels (XACC 222 and YACC 224) are used to calculate vibration and change in tilt levels and trip an alarm if either reaches a preset threshold level. The present invention also contemplates using the measured activity level to change the therapy state to either "interrupted", "active", or "out of sleeping position". The accelerometer and associated software are also used to control a secondary safety function so the integrity of the device is a consideration and any critical error must shut down therapy.

In an exemplary embodiment, the software implemented by the controller, which utilizes and verifies the accelerometer signals, has one or more of the following attributes:

Measures the vibration level.
Measures the relative change in tilt angle.
Changes the therapy state to "interrupted", when the activity alarms go beyond their trip values when therapy is "active".
Changes the therapy state to "active", if the activity alarms go below their trip values when therapy is "interrupted".
Changes the therapy state to "out of sleep position" if the activity alarms stay above their trip values when therapy is "interrupted".
Verifies that the average acceleration is within an expected range of g limits.
Verifies that the accelerometer's internal self-test function modulates the X and Y strain gauges as expected.
Verifies that the accelerometer power-flip test results in the expected output.

The ADXL311 accelerometer has an integral self test feature that allows a processor to dynamically verify the operation of the MEMS strain gauges and associated electronics. The ST or "Self Test" hardware input enables an internal electrostatic charge that applies a known force to the sensor that causes a change in the analog output signals. The controller's ACCTEST output toggles the ADXL311's ST input pin and verifies that the output has shifted the expected magnitude and direction. An alarm counter is incremented every time the accelerometer fails to deliver the expected output and decremented if the condition has returned to normal. If the alarm crosses a threshold defined a shutdown can result. The present invention contemplates that the accelerometer self test is performed on a periodic basis, such as every 10 seconds.

The ADXL311's maximum current draw is 1 mA (typically 0.4 mA), which is considerably higher than the controller. To conserve system power, the accelerometer is disabled when the vestibular stimulation system is not delivering therapy. Power is delivered to the accelerometer via a general purpose I/O pin ACCON 226, which is under software control. The primary intention for this feature is to limit the vestibular stimulation system's power dissipation, but it also provides the ability to verify that the accelerometer is the only device connected to the XACC and YACC circuit board nodes. The vestibular stimulation system accelerometer power-flip test toggles off the ADXL311's Vcc power and verifies that the average X and Y channel readings decrease an expected amount due to the outputs falling to zero volts. This test will trap a short or leakage path between the accelerometer analog outputs and any source that would cause the signals to drift upward.

Figure 25A:
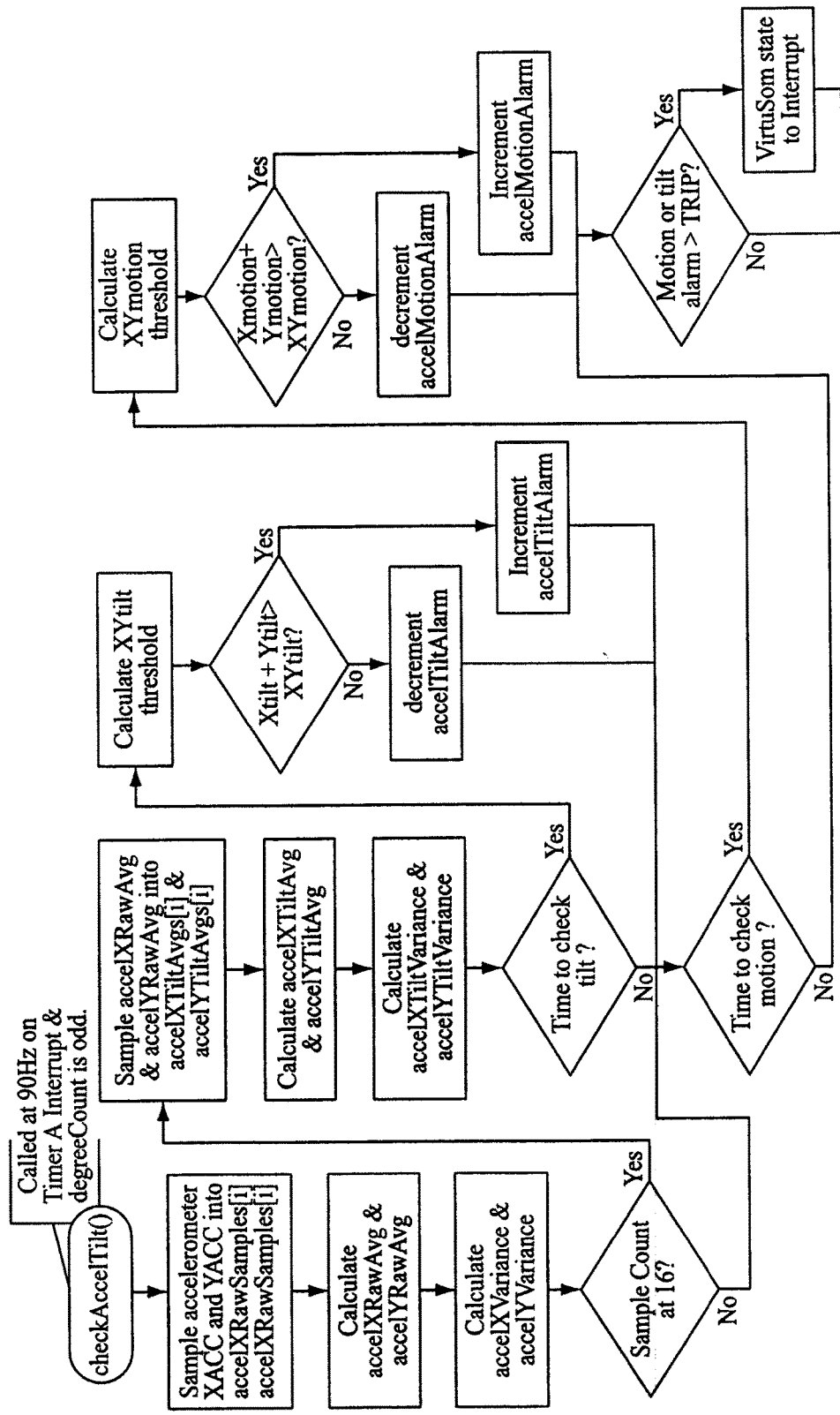
FIG. 25 is a flow chart of a process for controlling the stimulation therapy based on output of the accelerometer of FIG. 24.
Figure 25B:
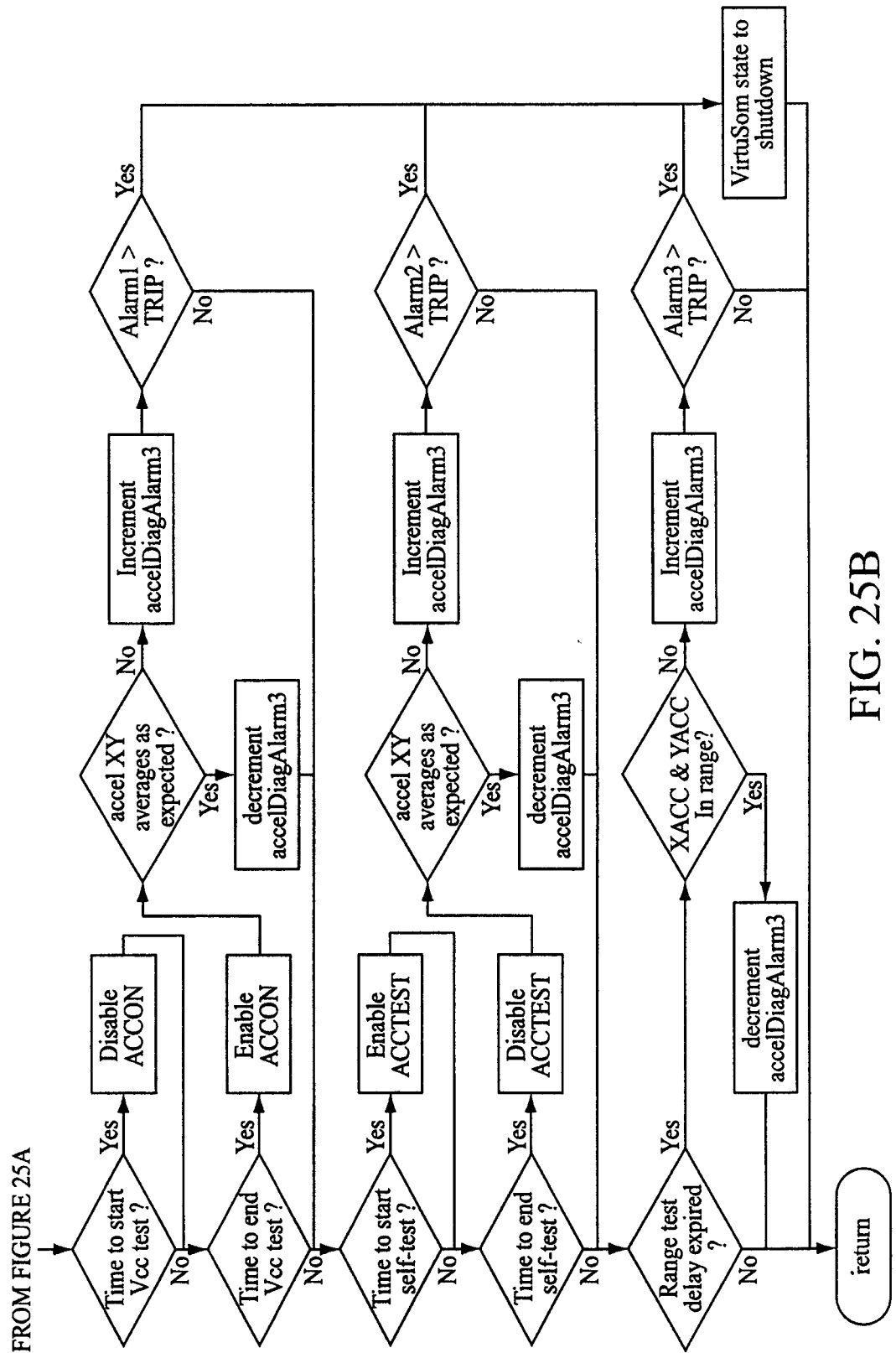

The VirtuSom's wake/activity monitor function is used to shutoff therapy if the user leaves the sleep position. A software function checkAccelTilt contains all the calculations and sensing logic used to manage the wake/activity algorithm. The software function checkAccelTilt is illustrated in FIG. 25.

The wake/activity monitor algorithm performs the following operations:

1) Acquires the raw XACC and YACC analog values into their respective circular arrays accelXRawSamples[ ] and accelYRawSamples[ ]. These arrays hold the values of the last 16 samples.

2) Calculates the averages of the 16 values in the arrays accelXRawSamples[ ] and accelYRawSamples[ ] as accelXRawAvg and accelYRawAvg using the formula:

$$accelRawAvg = \frac{\sum_i (accelRawSamples[i])}{ACCEL\_SAMPLES},$$

where: ACCEL_SAMPLES is equal to 16. The average of the raw value array represents the average tilt angle of the respective channel for the last 16 samples.

The wake/activity monitor algorithm further performs the following operations

3) Calculates the variances of the arrays as accelXVariance and accelYVariance using the formula:

$$accelVariance = \frac{\sum_i ABS(accelRawSamples[i] - accelRawAvg)}{ACCEL\_SAMPLES},$$

where: ABS=absolute value. The accelVariance represents the vibration motion of the respective channel for the last 16 samples.

4) Acquires, every 16, accelXRawAvg and accelYRawAvg value into their respective circular arrays accelXTiltAvgs[ ] and accelYTiltAvgs[ ].

5) Calculates the averages of the 16 values in the arrays accelXTiltAvgs[ ] and accelYTiltAvgs[ ] as accelXTiltAvg and accelYTiltAvg using the formula:

$$accelTiltAvg = \frac{\sum_i (accelTiltAvgs[i])}{ACCEL\_SAMPLES}$$

6) Calculates the variances of the arrays accelXTiltAvgs[ ] and accelYTiltAvgs[ ] as accelXTiltVariance and accelYTiltVariance using the formula:

$$accelTiltVariance = \frac{\sum_i ABS(accelTiltAvgs[i] - accelTiltAvg)}{ACCEL\_SAMPLES}$$

The accelTiltVariance represents the change in tilt of the respective channel for the last 256 samples.

7) Check if the sum of the accelXVariance+accelYVariance is greater than the threshold defined in ACCEL_XYMOTION and increment or decrement the accelMotionAlarm. ACCEL_XYMOTION is increased when the self test diagnostic is a portion of the vibration measurement.

8) Check if the sum of the accelXTiltVariance+accelXTiltVariance is greater than the threshold defined in ACCEL_XYTILT and increment or decrement the accelTiltAlarm. ACCEL_XYMOTION is increased when the self test diagnostic is a portion of the tilt measurement.

9) Check if the accelMotionAlarm or accelTiltAlarm is greater than the defined trip points ACCEL_MOTIONTRIP and ACCEL_TILTTRIP respectively. Set the gnVirtuSomState to STATE_INTERRUPT.

10) Continuously update the accelMotionAlarm and accelTiltAlarm values when the vestibular stimulation system is in STATE_INTERRUPT so that the state machine can switch to either OUT_OF_SLEEP or back into THERAPY_ACTIVE.

In an exemplary embodiment of the present invention, the wake/activity monitor measures both the vibration and relative change in tilt to determine if a therapy user is in motion. The change in tilt component responds to slow changes in either the X or Y accelerometer channels. The tilt parameter is sensitive to a user changing their sleep position, sitting upright, or standing. The vibration component responds to the higher frequency content in the accelerations that characterize a user in motion at a fixed tilt, hence the vibration measurement is sensitive to walking or running.

The accelerometer application software calculates the variance of the 16 values in the raw sample array to measure vibration. Whereas the variance of the 16 values in the tilt averages array represents the relative change in tilt over the sampling period. In practice, both variances are actually the sum total of the individual X and Y channel variances.

Figure 26:
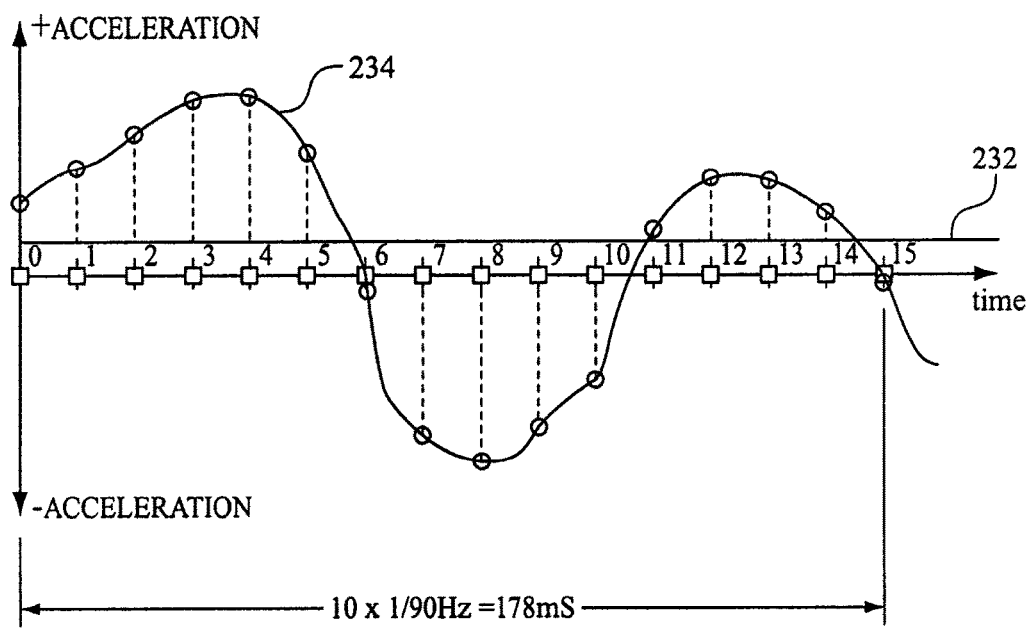
FIG. 26 is a graph showing how a variance of the acceleration raw sample array is calculated.

FIG. 26 illustrates how the variance of the raw sample array is calculated. A accelRawAvg 232 is calculated from the 16 accelRawSamples in the array. The accelRawAvg signal is shown as the horizontal dotted line in FIG. 26. A variance 234 of the accelRawSamples array is the average deviation of the samples from the mean. This is represented as the average of the magnitudes of the dashed vertical lines. Note that this calculation is performed independently on the X and Y axis.

The sampling time is the main difference between the vibration and tilt calculations. The 16 values used to calculate vibration sampled at 90 Hz for a total time of 178 ms. In FIG. 26, the period of the vibration is approximately 110 Hz. The vibration threshold constant ACCEL_VIB_THRESHOLD is currently set to 0.27 g/Hz which is a normalized acceleration of approximately 1.5 g over the sampling period. [0.27 g/Hz×¹/₁₇₈ mS].

Figure 27:
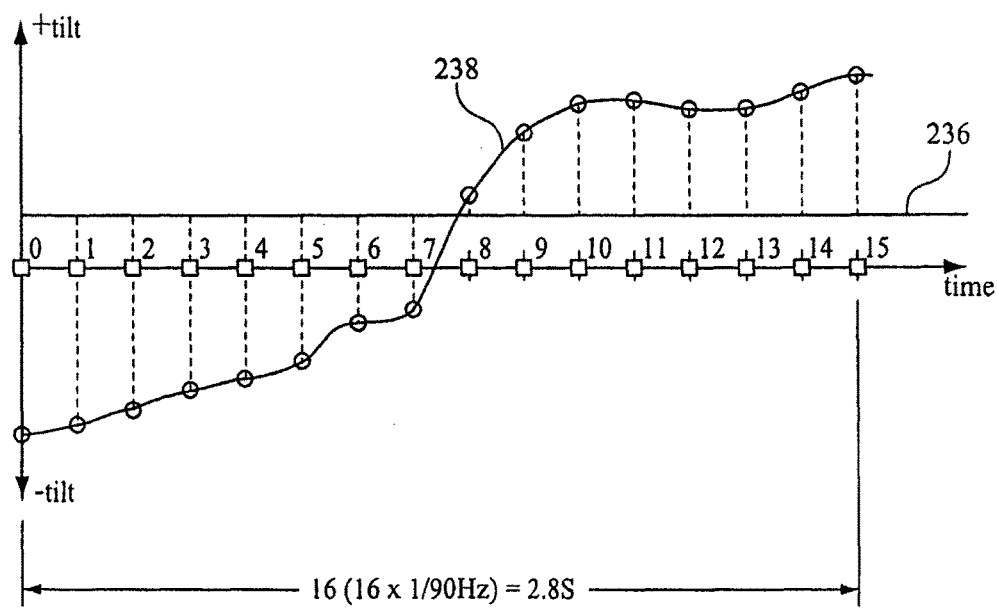
FIG. 27 is a graph showing how a variance of the tilt averages array is calculated.

FIG. 27 illustrates how the variance of the tilt averages array is calculated. Every $16^{th}$ accelRawAvg value is loaded into an array called "accelTiltAvgs", which represents the absolute tilt of the VirtuSom module over the sampling period. An accelTiltAvg 236 is calculated from the 16 accelTiltAvgs values in the array. The accelTiltAvg is shown as the horizontal dotted line in FIG. 27. A variance 238 of the accelTiltAvgs array is the average deviation of the samples from the mean. This is represented as the average of the magnitudes of the dashed vertical lines. Note that this calculation is also performed independently on the X and Y axis.

The 16 values used to calculate tilt are sampled 16 times at 178 ms for a total time of 2.8 seconds. In FIG. 27, the tilt angle changes direction from negative to positive. This is representative of a therapy user changing their side-to-side sleep position. A slowly changing tilt could also be representative of a user sitting upright, standing, or reclining backwards.

The tilt threshold constant ACCEL_TILT_THRESHOLD is currently set to 5.0 g/Hz which is a normalized acceleration of approximately 1.5 g for the sampling period. A change in tilt of 90° results in 1 g of displacement. So the tilt threshold is approximately equivalent to a user sitting upright in approximately 5 seconds or less. If a user moves any slower through the same angular displacement it will not be detected.

A walking or running user will have a very small change in tilt angle but a large vibration. A user rolling over in bed will have a large change in tilt but a potentially small vibration measurement. Therefore both the vibration and change in tilt measurements are required to effectively discriminate between a user changing and leaving their sleep position. The tilt and vibration thresholds are consistent with those used in the research of human gait analysis, location determination, and activity context awareness.

Figure 28:
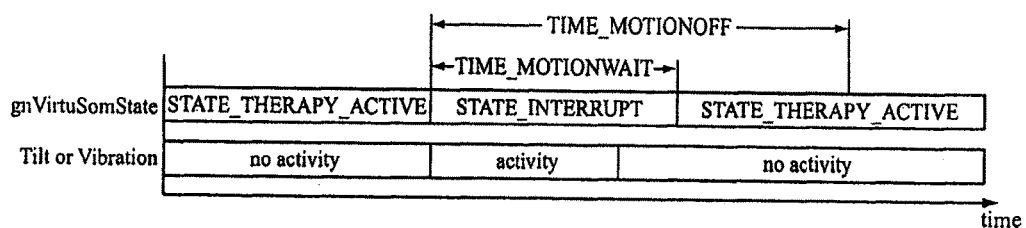
FIG. 28 is a timing diagram for a wake/activity monitor when the therapy is interrupted and restarted.
Figure 29:
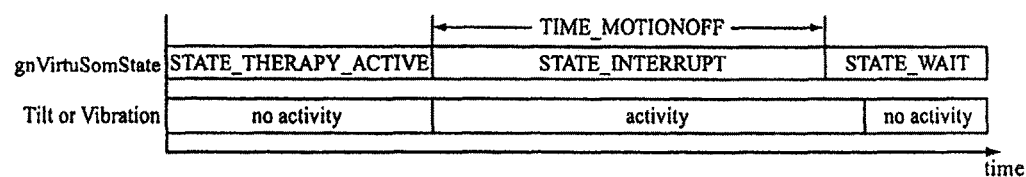
FIG. 29 is a timing diagram for the wake/activity monitor when therapy is interrupted and stopped.

As noted above, the state machine in the vestibular stimulation system uses the information provided by the accelerometer wake/activity monitor to disable and enable the stimulation therapy. The wake/activity function stop therapy when a user leaves their sleeping position. FIGS. 28 and 29 show the wake/activity function timing.

If a user's movement causes either the vibration or tilt alarm to reach their set threshold the gnVirtuSomState is set to STATE_INTERRUPT and therapy is interrupted for a minimum time set by the constant TIME_MOTIONWAIT. Therapy restarts if the user's activity drops below the alarm thresholds within the time set by the constant TIME_MOTIONOFF. Therapy is stopped and gnVirtuSomState is set to STATE_WAIT if activity is detected for a period of time longer than TIME_MOTIONOFF.

FIG. 28 shows the timing of the wake/activity monitor when therapy is interrupted and restarted. This situation is representative of a user adjusting their sleep position and activity was detected for a period less than TIME_MOTIONOFF. Therapy restarts when the activity alarms drop below their thresholds or after the interrupt time TIME_MOTIONWAIT, whichever is less. The timing constants TIME_MOTIONWAIT and TIME_MOTIONOFF are currently set to 4 and 8 seconds respectively.

FIG. 29 shows the timing of the wake/activity monitor when therapy is interrupted and stopped. This situation is representative of a user leaving their sleep position and activity was detected for a period greater than TIME_MOTIONOFF. The user must press a button to restart therapy.

B. Stimulation of User's That Are Not Lying Flat or Are Restless Sleepers

The vestibular stimulation control technique described in the '324 and '275 patents automatically turns off the stimulation therapy if the user begins sits up or stands. A conventional tilt switch, such as a mercury or ball-bearing switch, is used to detect when the user stands up. A problem with this type of arrangement is that some people sleep in the sitting position or with their torso in an upright or semi-recumbent or reclining position. This may cause a conventional device to shutdown or fail to delivery of stimulation even thought the user may still need/want the therapy. The present invention contemplates several techniques for providing stimulation therapy even to patients who tend to or prefer to sleep in a position in which their torso and/or head is not relatively flat.

In one embodiment, other parameters of the user are monitored, in addition to or instead of body position, to better determine when to give or not give the stimulation therapy to the user. For example, the present invention contemplates incorporating a heart rate or pulse rate sensor into the stimulation device. That is, in this embodiment, sensor 60 is a heart rate sensor. The heart rate information is used to estimate when the patient is asleep or at least relaxed so that stimulation therapy can be applied based on the sleep or relaxation determination, i.e., based on heart rate (whether or not the patient is deemed to be asleep or awake).

In an exemplary embodiment, the initial heart rate, i.e., when the device is initially activated (awake—with waking heart rate) is detected via heart rate sensor 60. Sleep or relaxation typically associated with sleep is detected when the heart rate lowers and flattens out over time. At this stage, the vestibular stimulation therapy can be discontinued. If the person becomes aroused and still wants to sleep, the device could then re-initiate and provide therapy. If the person were to stand up and begin to walk, the difference in heart rate between the relaxed state and walking is, at a minimum, a 15-20% increase. This increase can be detected and used to discontinue the stimulation therapy. Thus, this embodiment does not rely on a position sensor to determine when to allow or to discontinue the stimulation therapy.

Heart rate sensor 60 can be a skin-type sensor, ear clip or incorporated into a band (i.e. headband, wrist band, neckband). The present invention further contemplates that infrared monitoring could be used to measure changes in blood flow in the shallow capillary beds of the skin to determine heart rate.

Figure 23:
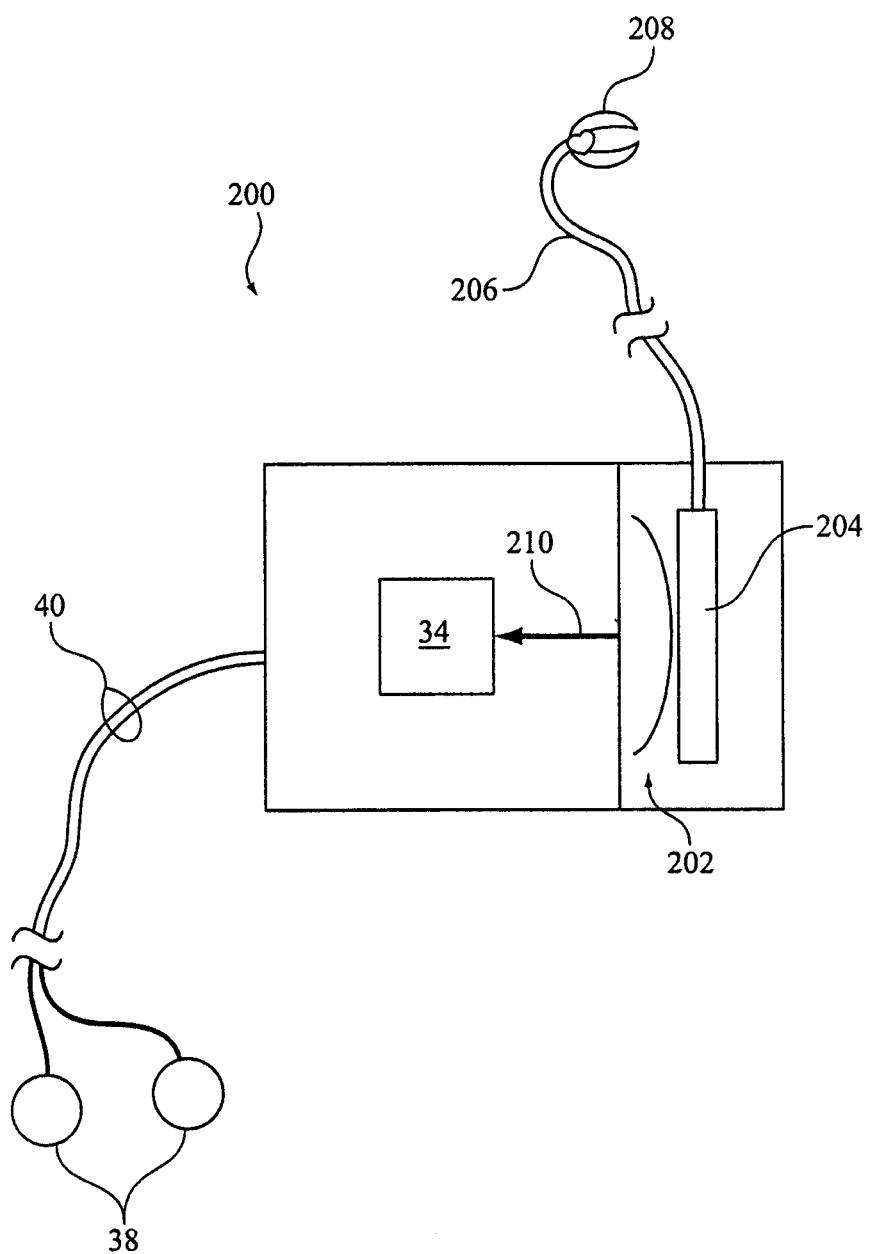
FIG. 23 is a schematic view of mechanical switching technique for use in controlling the delivery of the stimulation therapy according to the principles of the present invention.

In another embodiment of the present invention, which is shown in FIG. 23, a more mechanical or hardware based technique is used to account for patients that do not sleep in a supine position. In this embodiment, vestibular stimulation system 200 includes a small metal dome switch 202, e.g. Snapton's 5 mm WT-Series, PIN WTD05200 or WT05350, as sensor 60, in addition to or in place of a conventional tip-switch or tilt switch. An actuator 204 with a short tether 206 and a clip 208 is coupled to the dome switch. In an exemplary embodiment, actuator 204 engages dome switch 202 causing a signal 210 to be created. This signal can be caused, for example, by the actuator forcing the dome switch from an open state to a closed state. Signal 210 is provided to controller 34. As long as the controller receives this signal, the vestibular stimulation system is enabled; meaning that the vestibular system stimulation therapy can be provided to the patient.

Clip 208 is coupled to the patient, their clothing, the bedding, or any other item that would likely be moved if the patient moved from the sleeping area. If the patient moves from his sleeping location, regardless of the position in which they sleep (lying down, sitting, reclined, etc.) tether 206 pulls actuator 204 causing the dome switch to create a signal 210. This signal can be caused, for example, by the actuator releasing the dome switch so that it moves from a closed state to an open state. In other words, signal 210 can be discontinued. When this occurs, the vestibular stimulation system is disabled and the stimulation therapy is discontinued.

It should be understood that that the above-described mechanical or hardware based technique for controlling the stimulation therapy based on the position of the user is merely one example of the myriad of techniques that can be used for this purpose. For example, other switches and sensing devices, such as a thermal sensor, can be used to detect or monitor the position of the patient and control the stimulation therapy based on the result of the position monitoring. Clip 208 can be any type of device that can be secured to an item.

In a still further embodiment, the controller can be operated in such a way as to take into account a patient who does not sleep in a flat position, such as persons who sleep reclined or sitting up. For example, the present invention contemplates that a stimulation mode can be provided in which the output of a conventional tip-over switch is ignored, at least for one therapy session. In other words, it the patient desires to sleep in a position that would otherwise been deemed a non-flat position by a conventional tilt switch, a by-pass or override option can be given. The user may initiate this override to allow him or her to receive the stimulation therapy despite the output from the tilt switch. This by-pass or override mode can also be used for people who are restless sleepers; meaning that they tend to move around or change positions during sleep. Such relatively rapid position or orientation changes could erroneously be interpreted as someone moving about, i.e., not sleeping. The override mode would allow such a person to continue to receive therapy even in the presence of such movement.

C. Stimulation Based on Sleep State

The present invention also contemplates controlling the vestibular stimulation delivered to the user based on the sleep stage or state of the user. For example, the vestibular stimulation system can monitor whether the patient is in a REM state of sleep. If the user is in the REM state, the stimulation therapy is discontinued. If the user is not in the REM state, the stimulation therapy is delivered.

An exemplary embodiment of the present invention, the stimulation therapy is available over the during of the therapy window, e.g., during an 8-hour period on the system is activated. Upon actuation of a Therapy Request switch, such as button 54, and while the user is prone with the therapy electrodes properly connected an initiation stimulation therapy would is delivered for a predetermined period of time, such as 30 minutes, and then is stopped. The present invention contemplates using the stimulation system to detect whether the patient has entered or exited a REM stage using any conventional REM state detection technique. Exiting REM stage automatically restarts the stimulation therapy for another predetermined period of time, such as 30 minutes (or progressively less time as the therapy window progresses) if the therapy window hasn't expired. If the therapy window expires, the user removes the therapy electrodes, or the user rises, the therapy will stop and the therapy window will close.

As noted above, any conventional technique for detecting whether the user is in a REM state is contemplated by the present invention. This can include providing an EEG, EMG, EOG electrode or any combination thereof on the user and determine the presence or absence of REM sleep based on the output of the sensor.

In a slight twist, the present invention also contemplates using the vestibular stimulation system to wake the user. This can be accomplished by having the controller cause an arousing form or electrical stimulation to be provided to the user. Amplitude and frequencies for the stimulation signals provided to the vestibular system that are higher than that used to induce a rocking sensation are believed to elicit an arousal reaction in the patient. Thus, the vestibular stimulation system can be used as an alarm clock to wake the user at a particular time. Moreover, this arousal feature can be used to wake or prod the user in other circumstances. For example, the input to the system can be from a microphone, smoke detector, light detector, carbon monoxide detector, burglar alarm, or any other input source. The system can determine whether to wake the user based on this input. For example, if the input source is a microphone placed near a baby, the system can be programmed to wake the user if crying, gasping, or other noise is detected from the baby.

The present invention also contemplates using the vestibular stimulation system to wake the users after the user has had a predetermined amount of time in REM sleep. That is, the vestibular stimulation system could help induce REM sleep by inducing a rocking sensation in the user, track it by having the electrode assemblies function as sensing electrodes (or by providing separate sensing electrodes), and awaken the user when the amount of REM sleep reaches a predetermined threshold. The present invention contemplates that this threshold can be set or adjusted by the user, caregiver, device manufacture, or other authorized person.

D. Controlling the Stimulation Therapy Level

The present inventors observed that the voltage required to deliver a selected therapy current decreases over time. This drop in skin resistance seems to coincide with the user reporting a reduction in skin sensation (tingling, prickly). It was also believed that the delivered charge modulation to internal nerves (i.e. vestibular nerve) appeared to remain constant, as evidenced by the fact that evoked sensation (i.e. rocking/swaying) remained unchanged over time. This suggests that the reduction in skin sensation was a phenomena specific to the skin's sensory neurons (i.e. not a general lessening of all stimulation effectiveness), so that maximizing skin sensory comfort, i.e., minimizing tingling and prickly sensations, while providing an effective stimulation therapy, can be achieved by adjusting the stimulation energy delivered to the patient. More specifically, the stimulation level is ramped or changed from a lower level to a higher therapy level at the onset of the application of the stimulation energy. Providing the stimulation energy in this manner reduces the skin sensation associated with vestibular stimulation via electrodes in contact with the skin.

In one exemplary embodiment, the therapy current is ramped up to the user selected or set therapy level in relatively incremental steps. The duration of each step could be:

a) An arbitrary time compromising a time period that lies between the total time delay to full therapy level and the time needed to reduce skin sensation in a majority of users;

b) A dynamic duration determined by monitoring the resistance of the user. It has been observed that a lower incidence of skin sensation occurs when the peak voltage (electrode to electrode) is less than 7-9 volts. Also, this range can vary over time for each patient and can vary patient to patient. If the peak voltage required to deliver the present therapy current step drops an arbitrary amount below the initial peak voltage of the present therapy current step, the therapy current would be increased to the next step; or c) A combination of a) and b) above.

The present inventors also observed that "ramping" the stimulation level has a positive effect for users that have a higher tendency for motion sickness. Ramping or gradually increasing the therapy level seems to allow these users to experience higher therapy levels without or with less motion sensation associated discomfort.

In a further embodiment, the skin resistance determination, as described above, can be used to determine an optimal amount of therapy current/voltage to deliver to the user. For example, if the change of the measured resistance per unit time slows to a preset value or a percentage of an initial value, it can be determined that beyond that level of current, a higher proportion of voltage will be generated across the tissues under the skin per unit increase of therapy current (e.g., because the skin resistance has decreased). As the measured skin resistance drops, a progressively larger amount of current can be delivered to the patient, while keeping the voltage below a target control level so as to minimize skin sensation. The therapy voltage or current can then be limited to avoid exceeding a current/voltage threshold that would otherwise cause a skin sensation, while still providing a maximum amount of stimulation energy to the user.

The present invention also contemplates tracking the dynamic drop in skin resistance in order to predict the highest level of current that the device can successfully drive for the user (presuming a real-world device with power/voltage/current output limitations). For example, the system can monitor the resistance change at a preset level of current, or as the current is "ramping" to the set level, to determine if there is sufficient output power to continue raising the level. Thus, even if a user has a very high resistance, the system can drive the signal up to the point that power-out has reached its maximum (even if it is below the level requested). In the event that the resistance continues to drop or increases, the output level can be adjusted automatically or manually to a higher or lower level, thereby maximizing the power delivered to that user.

III. Other Features

In addition the functions and features noted above, the present invention contemplates including other capabilities in the vestibular stimulation system of the present invention. For example, control unit 70 can include memory for recording compliance information (usage of the stimulation system), status data, diagnostic information, or any other information regarding the stimulation therapy or the monitored variable. A memory chip or a removable memory device, such as USB memory stick, smart card, or disk can be used as the storage medium.

As a safety feature for the vestibular stimulation system, the present invention contemplates preventing the device from being used any time that it is connected to an AC power supply, for example, through the battery charger. To prevent this from happening, the mechanical interference between electrical lead 42, the terminals that connect to the electrical lead, battery charger terminal 44, and the battery charger lead, or any combination thereof are arranged such that electrical leads 40 cannot be connected to housing 42 at the same time that the batter charger is connected to terminal 44. In a further embodiment, the vestibular stimulation system determines when the battery charger is attached to the housing and prohibit the stimulation therapy from being administered or prevents the entire unit from operating during that time.

In the embodiments discussed above, the amount of stimulation energy provided to the user can be varied, for example, in a predetermine ramping fashion or is a dynamic manner, such as based on the user's skin resistance. However, the present invention also contemplates making the stimulation frequency selectable either by the user, or variable, for example based on the monitored condition of the user. It is likely that not everyone is optimally treated with the same frequency, i.e., rocking rate. Thus, the present invention contemplates providing the user or other authorized person to tune to stimulation frequency to the "sweet spot" for that user. This may be particularly useful in setting up the device for a particular user. The user or other person could manually adjust the stimulation frequency, for example remotely using a remote controller, to determine the frequency best suited for that individual user. Automatic adjustment of the frequency is also contemplated until the user's preferred frequency, i.e., the frequency that is best suited to induce relaxation in the subject, is identified.

In an exemplary embodiment of the present invention, the frequency of the stimulation energy is changed continuously over a given range of frequencies during a therapy session, such as sweeping the frequency between 0.1 Hz and 1.0 Hz. This is done because it is believed that the vestibular organs are most sensitive to changes in the environment, than to continuous inputs. By continuously altering the input therapy frequency, a continuously changing environment can be simulated, thereby keeping the vestibular pathways in a more constant state of flux. In short, the present invention contemplates utilizing a dynamic or predetermined program, which changes the character of the therapy waveform, such as its shape, amplitude, and/or frequency, during the therapy session, to increase the effectiveness of the therapy or comfort of the user. Of course, the user can also adjust a character of the therapy waveform by means of the input device, such as buttons 56 and 58, or via a remote controller.

As noted above, the electrical stimulation is applied to the user by means of two electrodes, one placed in each side of the user proximate to the left and right vestibular system. A time-varying energy, typically in the form of a sinusoidal current wave is applied to each electrode. In an exemplary embodiment, the sinusoidal waveforms applied to each electrode, i.e., to each side (vestibular system) of the user, are in phase, meaning that the same waveform is applied to both electrodes simultaneously.

The present invention also contemplates driving each electrode independently so that the waveform applied to one electrode is not identical to the waveform applied to the other electrode. In an exemplary embodiment, a sinusoidal waveform having a given amplitude and frequency, e.g., 2 mA and 0.5 Hz, is applied to one electrode, and a sinusoidal waveform having the same amplitude and frequency, but shifted in phase, is applied to the other electrode. In one embodiment, this phase shift is a 90° phase shift, so that a sinusoidal wave is applied to one electrode and a co-sinusiodal electrode is applied to the other. Of course, the amplitude and/or frequency of the waveform applied to one electrode can also be different from that applied to the other electrode in addition to or in place of the phase shift.

Because the vestibular stimulation system is worn by the user, the functions of other medical devices or monitors, such as those found in portable sleep screeners can also be including the vestibular stimulation system. For example, oximetry, airflow monitoring, EEG recording, and any other functions typically performed by patient monitors can be included in the vestibular stimulation system of the present invention.

The present invention also contemplates providing an auditory output to ear phones or speakers. Such ear phones can be incorporated into or otherwise connected to electrodes 38 and/or electrical leads 40. The auditory output can include user feedback, information regarding the stimulation device and/or therapy, tranquil sounds, music, or any other sounds. In a further embodiment, the sounds delivered to the user are synchronized with the stimulation delivered to the vestibular system to enhance the effect of the vestibular stimulation.

The present invention contemplates that the vestibular stimulation system can be used in combination with other medical therapy devices. Thus, the vestibular stimulation therapy provided by vestibular stimulation system 30 can be used in combination with other medical treatments or therapies. In an exemplary embodiment, the patient receives both a vestibular stimulation therapy to assist him or her in falling asleep or remaining asleep and a pressure support therapy to treat a breathing disorder.

Examples of pressure support therapies include applying a continuous positive air pressure (CPAP) to the patient's airway. This positive pressure effectively "splints" the airway, thereby maintaining an open passage to the lungs. Example of CPAP devices that provide this therapy are the REMstar® family of CPAP devices manufactured by Respironics, Inc. of Pittsburgh, Pa.

Another form of pressure support therapy involves providing a bi-level positive pressure therapy to the patient. In this treatment therapy, the pressure of fluid delivered to the patient's airway varies or is synchronized with the patient's breathing cycle to maximize the therapeutic effect and comfort to the patient. During inspiration, the patent receives an inspiratory positive airway pressure (IPAP), and during expiration, the patient receives an expiratory positive airway pressure (EPAP) that is lower than the IPAP. An example of a pressure support device that provides "bi-level" pressure support, in which a lower pressure is delivered to that patient during the patient's expiratory phase than during the inspiratory phase, is the BiPAP® family of devices manufactured and distributed by Respironics, Inc. of Pittsburgh, Pa.

It is further known to provide a respiratory treatment therapy in which the pressure provided to the patient is automatically adjusted based on the detected conditions of the patient, such as whether the patient is snoring or experiencing an apnea, hypopnea, or snoring. This respiratory treatment technique is referred to as an auto-titration type of pressure support, because the pressure support device seeks to provide a pressure to the patient that is only as high as necessary to treat the disordered breathing. An example of a device that adjusts the pressure delivered to the patient based on whether or not the patient is snoring is the REMstar® Auto device manufactured and distributed by Respironics, Inc.

Other pressure support systems that offer other modes of providing positive pressure to the patient that are suitable for use with the present invention include a proportional assist ventilation (PAV®) mode of pressure support that provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV mode.

Proportional positive airway pressure (PPAP) devices deliver breathing gas to the patient based on the flow generated by the patient. U.S. Pat. Nos. 5,535,738; 5,794,615; 6,105,575; 6,609,517; and 6,932,084, (collectively referred to as "the PPAP patents") the contents of which are incorporated herein by reference, teach a pressure support device capable of operating in a PPAP mode. Examples a device that adjusts the pressure delivered to the patient based on the patient's respiratory flow is the REMstar® Pro, Plus, or Auto with C-Flex™ or Bi-Flex® devices manufactured and distributed by Respironics, Inc. The term "C-Flex" refers to a device that provides a CPAP respiratory treatment therapy in which the pressure delivered to the patient is reduced in proportion to flow during expiration. The term "Bi-Flex" refers to a device that provides a bi-level respiratory treatment therapy in which either the IPAP or EPAP pressures are further reduced in proportion to flow.

It is also known to provide a combination of such respiratory therapies. For example, a CPAP device with C-Flex can be auto-titrating, such as REMstar® Auto with C-Flex™, so that the CPAP pressure varies during a treatment session based on the monitored condition of the patient. Similarly, a bi-level device with Bi-Flex can be auto-titrating, such as Bi-PAP® Auto with Bi-Flex™, so that the IPAP and EPAP pressures vary during a treatment session based on the monitored condition of the patient. In an auto titrating bi-level device, the difference between IPAP and EPAP, which is referred to as the pressure support (PS), can vary according to the auto-titration algorithm or it can be held constant depending on how the device is configured.

Other medical therapy devices suitable for use with the vestibular stimulation system of the present invention include phototherapy devices, nebulizers, transcutaneous neural stimulators (TENS) devices, and invasive or non-invasive drug delivery devices.

The present invention contemplates that the vestibular stimulation system include embedded software that is adapted to perform built-in self tests (BIST) at power-on, power-down, and during operation. Table 1 below lists examples of tests that are contemplated by the present invention.

TABLE 1

| Test | Description |
| --- | --- |
| Therapy Signal Above Tolerance Test | This test checks that the therapy output current doesn't exceed 150 +/− 10% of the expected output or 150 +/− 10% expected peak. A fault is declared if the measured current exceeds 150 +/− 10% of current level's peak +/−0.03 or if the measured current exceeds 150 +/− 10% of the expected current for 0.25 +/− 0.03 seconds when the expected current is greater than 90 +/− 10% of a level 1 peak. If the test fails, the device enters Off Mode. |
| Therapy Signal Below Tolerance Test | This test checks that the therapy output current is at least 50 +/− 10% of the expected output. A fault is declared if the measured current drops below 50 +/− 10% of the expected current for 0.25 +/− 0.03 seconds when the output voltage is less than the minimum clipped voltage of 24.4 +/− 2.4 VDC. If the test fails, the device enters Off Mode. |
| High Resistance Test | This test evaluates the output voltage and current to ensure the patient load is not out of range. A fault is declared if the measured current drops below 50 +/− 10% of the expected current for 0.25 +.− 0.03 seconds when the output voltage greater than or equal to the minimum clipped voltage of 24.4 +/− 2.4 VDC. If the test fails, the device enters a Standby Mode. |
| Electrodes Open Test | This test evaluates the output voltage and current to ensure the electrodes are not open. A fault is declared if the measured current is less than or equal to 0.054 +/− 0.005 mA for 0.25 +/− 0.03 seconds when the output voltage greater than or equal to the minimum clipped voltage of 24.4 +/− 2.4 VDC. If the test fails, the device enters the Standby Mode. |
| Shorted Output Stage Test | This test evaluates the output voltage and current to ensure the Output Stage is not shorted. A fault is declared if the output current is within tolerance and 500 ohm load is placed across the electrode output for 0.50 +/− 0.05 seconds. This fault will not occur for a load of 8 KΩ or higher. If the test fails, the device enters an Off Mode. |
| Leakage Test | The test checks that the return current is equal to the output current. A fault is declared if the output current is greater or equal to 0.10 +/− 0.01 mA and the output current exceeds the feedback current by 0.30 +/− 0.03 mA or more for 0.25 +/− 0.03 seconds. If the test fails, the device enters the Off Mode. |

TABLE 1-continued

| Test | Description |
|---|---|
| Net DC Current Test | This test checks that the positive and negative phases of the therapy output are supplying equal current. A fault is declared after two complete therapy signal periods if the absolute difference between the positive half cycles and the negative half cycle exceeds the equivalent of 0.025 +/− 0.003 mA DC over 8 cycles. If the test fails, the device enters the Off Mode. |
| H-Bridge Test | Prior to delivering therapy, this test checks that an H-Bridge can be opened and closed. This test protects against an H-Bridge fault condition that would provide a rectified therapy signal to the patient, e.g. the H-Bridges switches fail so that therapy is always driven on the Left Electrode and returned on the Right Electrode. |
| Therapy Zero Test | This test checks that the therapy output is indeed inactive when expected. A fault is declared if the output voltage exceeds 0.10 +/− 0.01 VDC and the feedback current exceeds 0.020 +/− 0.002 mA for 0.25 +/− 0.03 seconds. If the test fails, the device enters the Off Mode. |
| Accelerometer Power Test | This test is run at the beginning of therapy. Before the accelerometer is powered up, all outputs are read and verified to be below an off state threshold. After the accelerometer is powered up all outputs are read and verified to be within acceptable range. If the test fails, the device enters the Off Mode. |
| Accelerometer Self Test | This test is run every 10 seconds during therapy. The software reads both outputs and then enables the accelerometer's self test. The self test adds a known offset to both axis outputs. The software reads both outputs and disables the self test. The self test readings of both axis outputs must have increased by 50 to 150% of the known offset compared to the pretest outputs or the test fails. If the test fails 3 times consecutively (30 seconds), the device enters the Off Mode. |
| Accelerometer Range Test | This test is run whenever the other accelerometer tests are not running. The test verifies that both axes outputs are within +/−4 g. If either axis falls out of this range for 0.50 +/− 0.05 seconds, the device enters the Off Mode. |

The present invention also contemplates that the system can carry out additional tests that are standard for electronic equipment, such as memory tests, watchdog tests, clock tests, stuck user interface switch tests, etc.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. One of skill in the art will easily recognize additional ways of implementing embodiments within the categories described hereinabove.

What is claimed is:

1. A method of providing vestibular stimulation to a user through stimulation of a vestibular system of the user, the method comprising:
   providing a vestibular stimulation system comprising:
      a housing configured to extend over the top of the head of the user, the housing comprising a first end portion and a second end portion;
      a power supply disposed in the housing;
      one or more sensors disposed in the housing, the one or more sensors comprising an accelerometer configured to generate output signals that convey information related to vibration and tilt level of the accelerometer caused by the user;
      a controller disposed in the housing and operatively coupled to the power supply;
      two arms coupled to the housing, wherein individual ones of the two arms comprise a first end and a second end, wherein the first ends of the two arms are coupled to the housing, and wherein the two arms are biased toward one another to provide a clamping force on the user's head such that one or more electrical conductors are positioned and/or maintained at a predetermined position on the user; and
      an electrode assembly having the one or more electrical conductors, the electrode assembly being coupled to individual ones of the second ends of the two arms;
   mounting the housing on the user;
   controlling, via the controller, the stimulation of the vestibular system of the user, during a vestibular stimulation therapy provided to the user by the vestibular stimulation system, through delivery of energy from the power supply to the electrode assembly based on the output signals;
   changing, via the controller, a therapy state of the vestibular stimulation therapy from an active state to an interrupted state, responsive to either the vibration or the tilt level breaching a first threshold;
   changing, via the controller, the therapy state of the vestibular stimulation therapy from the interrupted state to the active state, responsive to the vibration or tilt level ceasing to breach the first threshold before an interruption timer breaches a second threshold; and
   changing, via the controller, the therapy state of the vestibular stimulation therapy from the interrupted state to a stopped state, responsive to the vibration or tilt level continuing to breach the first threshold after the interruption timer breaches the second threshold, wherein, in the active state, the vestibular stimulation therapy is delivered to the user, wherein, in the interrupted state, the vestibular stimulation therapy is discontinued to the user when either the vibration or the tilt level breaches the first threshold and before the interruption timer breaches the second threshold, and wherein, in the stopped state, the vestibular stimulation therapy is discontinued to the user when either the vibration or the tilt level continues to breach the first threshold and after the interruption timer breaches the second threshold.

2. The method of claim 1, wherein delivering the stimulation includes delivering a sinusoidal wave having a frequency, wherein the stimulation of the vestibular system includes changes in one or more features of the delivery of the energy to the electrode assembly, and wherein the changes in the one or more features of the delivery of the energy include a sweep of the frequency of the sinusoidal wave in a range from 0.1 Hz to 1 Hz.

3. The method of claim 1, wherein the vestibular stimulation therapy is provided, by the vestibular stimulation system, even to a user who tends to sleep in a position in which their torso and/or head is not resting flat.

4. The method of claim 1, further comprising:
determining whether the user is deemed awake; and
controlling the delivery of the stimulation based on whether the user is deemed awake.

5. The method of claim 1, further comprising controlling the delivery of energy from the power supply to the electrode assembly such that the stimulation provided to the vestibular system of the user promotes relaxation and/or waking in the user.

6. The method of claim 1, further comprising changing a parameter associated with the stimulation over time.

7. The method of claim 6, wherein the parameter is a frequency, shape, amplitude, power, phase, or any combination thereof.

8. The method of claim 1, wherein the vestibular stimulation system further comprises:
an auditory output device coupled to the housing and a display disposed on an exterior surface of the housing, wherein the method further comprises:
providing, via the auditory output device, auditory output to the user through delivery of an auditory signal; and
providing, via the display, visual information regarding operation of the vestibular stimulation system.

9. The method of claim 1, wherein delivering the stimulation includes providing energy from a battery, an inductive field receiving element, or both disposed in the housing.

10. The method of claim 1, further comprising providing a pressure support therapy, a sound therapy, an aroma therapy, a circadian rhythm therapy, or any combination thereof.

11. A vestibular stimulation system configured to provide stimulation of a vestibular system of a user, comprising:
a housing configured to extend over the top of the head of the user;
a power supply disposed in the housing;
one or more sensors disposed in the housing, the one or more sensors comprising an accelerometer configured to generate output signals that convey information related to vibration and tilt level of the accelerometer caused by the user;
a controller disposed in the housing and operatively coupled to the power supply;
two arms coupled to the housing, wherein individual ones of the two arms comprise a first end and a second end, wherein the first ends of the two arms are coupled to the housing, and wherein the two arms are biased toward one another to provide a clamping force on the user's head such that one or more electrical conductors are positioned and/or maintained at a predetermined position on the user; and
an electrode assembly having the one or more electrical conductors, the electrode assembly being coupled to individual ones of the second ends of the two arms, wherein the controller is configured to:
(a) control the stimulation of the vestibular system of the user, during a vestibular stimulation therapy provided to the user by the vestibular stimulation system, through delivery of energy from the power supply to the electrode assembly based on the output signals from the one or more sensors;
(b) change a therapy state of the vestibular stimulation therapy from an active state to an interrupted state, responsive to either the vibration or the tilt level breaching a first threshold;
(c) change the therapy state of the vestibular stimulation therapy from the interrupted state to the active state, responsive to the vibration or tilt level ceasing to breach the first threshold before an interruption timer breaches a second threshold; and
(d) change the therapy state of the vestibular stimulation therapy from the interrupted state to a stopped state, responsive to the vibration or tilt level continuing to breach the first threshold after the interruption timer breaches the second threshold, wherein, in the active state, the vestibular simulation therapy is delivered to the user, wherein, in the interrupted state, the vestibular stimulation therapy is discontinued to the user when either the vibration or the tilt level breaches the first threshold and before the interruption timer breaches the second threshold, and wherein, in the stopped state, the vestibular stimulation therapy discontinued to the user when either the vibration or the tilt level continues to breach the first threshold and after the interruption timer breaches the second threshold.

12. The system of claim 11, wherein the electrode assembly includes a first electrode and a second electrode, and wherein the controller controls the stimulation of the vestibular system of the user through the delivery of energy from the power supply to the first electrode in a first sinusoidal waveform and to the second electrode in a second sinusoidal waveform such that the first sinusoidal waveform and the second sinusoidal waveform have the same frequency and are shifted in phase.

13. The system of claim 12, wherein the first sinusoidal waveform and the second sinusoidal waveform are shifted in phase by 90 degrees.

14. The system of claim 11, wherein the controller is further configured to control the stimulation of the vestibular system of the user through the delivery of energy to the electrode assembly as a sinusoidal wave having a frequency, wherein the controller is further configured to control the stimulation of the vestibular system to include changes in one or more features of the delivery of the energy to the electrode assembly, and wherein the changes in the one or more features of the delivery of the energy include a sweep of the frequency of the sinusoidal wave in a range from 0.1 Hz to 1 Hz.

15. The system of claim 11, wherein the accelerometer is a multi-axis accelerometer that is configured to measure relative changes in the tilt level and the vibration of the user.

16. The system of claim 11, wherein the accelerometer is a two-axis analog micro electro mechanical system (MEMS) that is configured to measure relative changes in the vibration and the tilt level.

17. The system of claim 16, wherein the MEMS accelerometer measures dynamic and static acceleration such that the output signals are useable to determine roll and pitch angles of the housing.

18. The system of claim 11, wherein the controller is adapted to determine whether the user is deemed awake, wherein the controller controls the delivery of energy to the user based on whether the user is deemed awake.

19. The system of claim 11, wherein the controller controls the delivery of energy from the power supply to the electrode assembly such that stimulation energy provided to the vestibular system of the user promotes sleep and/or relaxation or waking in the user.

20. The system of claim 11, wherein the controller is adapted to change a parameter associated with the vestibular stimulation therapy over time.

21. The system of claim 20, wherein the parameter is a frequency, shape, amplitude, power, phase, or any combination thereof.

22. The system of claim 11, further comprising:
- a display disposed on an exterior surface of the housing, wherein the display is adapted to provide visual information regarding operation of the vestibular stimulation system; and
- an auditory output device coupled to the housing, wherein the auditory output device is configured to provide auditory output to a user through delivery of an auditory signal.

* * * * *